(12) United States Patent
Kaneko

(10) Patent No.: US 11,553,877 B2
(45) Date of Patent: Jan. 17, 2023

(54) HEALTH MANAGEMENT APPARATUS, METHOD FOR OPERATING HEALTH MANAGEMENT APPARATUS, AND PROGRAM FOR OPERATING HEALTH MANAGEMENT APPARATUS

(71) Applicant: FUJIFILM CORPORATION, Tokyo (JP)

(72) Inventor: Yasuhisa Kaneko, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 420 days.

(21) Appl. No.: 16/809,552

(22) Filed: Mar. 5, 2020

(65) Prior Publication Data

US 2020/0305790 A1   Oct. 1, 2020

(30) Foreign Application Priority Data

Mar. 29, 2019   (JP) .............................. JP2019-067748

(51) Int. Cl.
*A61B 5/00* (2006.01)
*A61B 5/06* (2006.01)
(Continued)

(52) U.S. Cl.
CPC .............. *A61B 5/4872* (2013.01); *A61B 5/06* (2013.01); *A61B 5/4504* (2013.01);
(Continued)

(58) Field of Classification Search
None
See application file for complete search history.

(56) References Cited

U.S. PATENT DOCUMENTS 10,045,751 B2 *  8/2018  Okusu .................... A61B 6/465
11,062,735 B2 *  7/2021  Taneda ................. G11B 27/007
(Continued)

FOREIGN PATENT DOCUMENTS

JP   2004-329225 A   11/2004
JP   2005-245669 A    9/2005
(Continued)

OTHER PUBLICATIONS

English language translation of the following: Office action dated Dec. 7, 2021 from the JPO in a Japanese patent application No. 2019-067748 corresponding to the instant patent application. This office action translation is submitted now in order to supplement the understanding of the cited references which are being disclosed in the instant Information Disclosure Statement.
(Continued)

*Primary Examiner* — Santiago Garcia
(74) *Attorney, Agent, or Firm* — Solaris Intellectual Property Group, PLLC

(57) ABSTRACT

A CPU of a health management apparatus functions as an acquisition unit, a first derivation unit, and a screen output control unit. The acquisition unit acquires a body-fat percentage which is an obesity parameter indicating the degree of obesity of a target pet and bone density which is a bone parameter indicating the degree of bone strength of the target pet. The first derivation unit derives health conditions of the target pet on the basis of a correlation between the body-fat percentage and the bone density. A screen output control unit performs control to output a medical examination result display screen on which the health conditions are displayed.

13 Claims, 28 Drawing Sheets

(51) Int. Cl.
 *G16H 20/60* (2018.01)
 *G16H 40/67* (2018.01)
 *G16H 50/20* (2018.01)
(52) U.S. Cl.
 CPC ............ *A61B 5/4509* (2013.01); *A61B 5/742* (2013.01); *G16H 20/60* (2018.01); *G16H 40/67* (2018.01); *G16H 50/20* (2018.01); *A61B 2503/40* (2013.01)

(56) References Cited

U.S. PATENT DOCUMENTS

| | | | |
|---|---|---|---|
| 2004/0202652 A1* | 10/2004 | Karsenty | A61K 38/55 424/143.1 |
| 2005/0177060 A1 | 8/2005 | Yamazaki et al. | |
| 2007/0207468 A1* | 9/2007 | Hoffman | C12Q 1/6883 435/6.1 |
| 2012/0029380 A1* | 2/2012 | Ki Chul | A61B 5/0537 600/547 |
| 2013/0121461 A1 | 5/2013 | Toll et al. | |
| 2015/0105651 A1 | 4/2015 | Zheng | |
| 2016/0081642 A1* | 3/2016 | Okusu | A61B 6/4452 715/709 |
| 2016/0081650 A1* | 3/2016 | Okusu | A61B 6/465 715/826 |
| 2016/0088284 A1* | 3/2016 | Sareen | G06T 3/60 348/47 |
| 2016/0213560 A1* | 7/2016 | Sturdivant | A61N 1/39044 |
| 2016/0247017 A1* | 8/2016 | Sareen | G06T 7/60 |
| 2017/0238819 A1* | 8/2017 | Waller | A61B 5/4875 |
| 2018/0277159 A1* | 9/2018 | Taneda | A61B 6/4405 |
| 2020/0265936 A1* | 8/2020 | Ishikawa | G06F 3/0484 |

FOREIGN PATENT DOCUMENTS

| | | |
|---|---|---|
| JP | 2015-038734 A | 2/2015 |
| JP | 2017-500675 A | 1/2017 |

OTHER PUBLICATIONS

English language translation of the following: Decision of Refusal dated Jun. 7, 2022 from the JPO in a Japanese patent application No. 2019-067748 corresponding to the instant patent application.

* cited by examiner

FIG. 17

HCCT

| PREVIOUS REGION | CURRENT REGION | CHANGE IN HEALTH CONDITIONS |
|---|---|---|
| R_A1 | R_A2 | STILL HEALTHY |
| R_A2 | R_A1 | |
| R_A1, R_A2 | R_B | PROGRESS OF OBESITY DUE TO OVEREATING |
| R_A1, R_A2 | R_C | PROGRESS OF OBESITY DUE TO OVEREATING |
| R_A1, R_A2 | R_D1, R_D2 | PROGRESS OF OSTEOPOROSIS WITH AGING |
| R_A1, R_A2 | R_E | PROGRESS OF OBESITY AND OSTEOPOROSIS DUE TO HORMONE IMBALANCE |
| ⋮ | ⋮ | ⋮ |
| R_B | R_F | THERE IS POSSIBILITY OF HORMONE IMBALANCE |
| ⋮ | ⋮ | ⋮ |
| R_C | R_E | THERE IS POSSIBILITY OF DIABETES DUE TO OVEREATING |
| ⋮ | ⋮ | ⋮ |
| R_B | R_A2 | IMPROVEMENT OF OBESITY |
| ⋮ | ⋮ | ⋮ |

| MEDICAL EXAMINATION RESULT REPORT |
|---|
| PET INFORMATION |
| Mr. JOHN, FIVE YEARS OLD, MALE, LABRADOR RETRIEVER |
| BODY-FAT PERCENTAGE-BONE DENSITY PLOT |

(Plot showing body-fat percentage vs. bone density with points IP_LT, IP_TT, IP_SP, HCC_SP, and region CR; labels 92, 97)

SIMILAR PET DISPLAY

| HEALTH CONDITIONS | CHANGE IN HEALTH CONDITIONS |
|---|---|
| THERE IS POSSIBILITY OF HORMONE IMBALANCE OR THERE IS POSSIBILITY OF DIABETES DUE TO OBESITY | THERE IS POSSIBILITY OF HORMONE IMBALANCE |

| ADVICE |
|---|
| LET'S REVIEW DIETARY CONTENT OR WALK TO IMPROVE HEALTH |

DISPLAY SWITCHING

FIG. 30

| MEDICAL EXAMINATION RESULT REPORT |
|---|
| PET INFORMATION |
| Mr. JOHN, FIVE YEARS OLD, MALE, LABRADOR RETRIEVER |
| BODY-FAT PERCENTAGE-BONE DENSITY PLOT |

(plot with axes BODY-FAT PERCENTAGE and BONE DENSITY; callout "CALORIC RESTRICTION, MEDICINE A"; labels IP_LT, IP_TT, IP_BP, HCC_SP, 92, 107, 108, CR)

SIMILAR PET DISPLAY

| HEALTH CONDITIONS | CHANGE IN HEALTH CONDITIONS |
|---|---|
| THERE IS POSSIBILITY OF HORMONE IMBALANCE OR THERE IS POSSIBILITY OF DIABETES DUE TO OBESITY | THERE IS POSSIBILITY OF HORMONE IMBALANCE |

ADVICE

LET'S REVIEW DIETARY CONTENT OR WALK TO IMPROVE HEALTH

DISPLAY SWITCHING

HEALTH MANAGEMENT APPARATUS, METHOD FOR OPERATING HEALTH MANAGEMENT APPARATUS, AND PROGRAM FOR OPERATING HEALTH MANAGEMENT APPARATUS

CROSS-REFERENCE TO RELATED APPLICATIONS

The present application claims priority under 35 U.S.C. § 119 to Japanese Patent Application No. 2019-067748 filed on Mar. 29, 2019. The above application is hereby expressly incorporated by reference, in its entirety, into the present application.

BACKGROUND

1. Technical Field

The technology of the present disclosure relates to a health management apparatus, a method for operating the health management apparatus, and a program for operating the health management apparatus.

2. Description of the Related Art

JP2005-245669A discloses a health management apparatus for managing the health conditions of a subject. The health management apparatus disclosed in JP2005-245669A acquires a plurality of parameters indicating the body composition of the subject, such as a body-fat percentage, bone mass, and bone density, and displays and outputs a graph indicating a time-series change in each parameter.

SUMMARY

Obesity is a cause of various lifestyle-related diseases. In addition, the weakening of bones causes the body to weaken. For example, the weakening of bones causes a fracture and forces a person to receive a nursing care. Therefore, an obesity parameter indicating the degree of obesity of a subject, such as a body-fat percentage, and a bone parameter indicating the degree of bone strength of the subject, such as bone mass or bone density, are particularly important parameters.

Recently, with an increase in health consciousness, there is a demand for knowing health conditions referring to both the obesity parameter and the bone parameter which are important parameters as described above. However, in the related art, as in the health management apparatus disclosed in JP2005-245669A, the health conditions are separately evaluated by the obesity parameter and the bone parameter. Therefore, it is difficult to respond to the demand for knowing the health conditions referring to both the obesity parameter and the bone parameter.

An object of the technology according to the present disclosure is to provide a health management apparatus, a method for operating the health management apparatus, and a program for operating the health management apparatus which can notify health conditions referring to both an obesity parameter and a bone parameter.

In order to achieve the object, according to the present disclosure, there is provided a health management apparatus comprising: an acquisition unit that acquires an obesity parameter indicating a degree of obesity of a target subject and a bone parameter indicating a degree of bone strength of the target subject; a first derivation unit that derives a health condition of the target subject on the basis of a correlation between the obesity parameter and the bone parameter; and an output control unit that performs control to output the health condition.

Preferably, the health management apparatus further comprises a reading unit that reads, from a storage unit, a health condition table in which the health condition corresponding to each of a plurality of divided regions obtained by dividing a coordinate region in which the obesity parameter is disposed on one of a vertical axis and a horizontal axis and the bone parameter is disposed on the other axis has been registered and outputs the health condition table to the first derivation unit. Preferably, the first derivation unit derives the health condition corresponding to the divided region in which an intersection point of the obesity parameter and the bone parameter of the target subject is present from the health condition table.

Preferably, the output control unit performs control to output the coordinate region including the intersection point of the obesity parameter and the bone parameter of the target subject.

Preferably, the health management apparatus further comprises a second derivation unit that derives a change in the health condition of the target subject on the basis of a correlation between a previous obesity parameter and a previous bone parameter of the target subject and a correlation between a current obesity parameter and a current bone parameter of the target subject. Preferably, the output control unit performs control to output the change in the health condition.

Preferably, the reading unit reads, from the storage unit, a health condition change table in which a change in the health condition corresponding to a previous region that is the divided region including the intersection point of the previous obesity parameter and the previous bone parameter and a current region that is the divided region including the intersection point of the current obesity parameter and the current bone parameter has been registered and outputs the health condition change table to the second derivation unit and the second derivation unit derives the change in the health condition corresponding to the previous region and the current region of the target subject from the health condition change table.

Preferably, the output control unit performs control to output the coordinate region including the intersection point of the previous obesity parameter and the previous bone parameter of the target subject and the intersection point of the current obesity parameter and the current bone parameter of the target subject.

Preferably, the health management apparatus further comprises a first search unit that searches for a similar subject having a similar change in the health condition to the target subject. Preferably, the output control unit performs control to output a change in the health condition of the similar subject.

Preferably, the output control unit performs control to output the coordinate region including the intersection point of the obesity parameter and the bone parameter of the similar subject in addition to the intersection point of the previous obesity parameter and the previous bone parameter of the target subject and the intersection point of the current obesity parameter and the current bone parameter of the target subject.

Preferably, the health management apparatus further comprises a second search unit that searches for prescription information on an improved subject whose health condition is inversely changing to improvement in a case in which content of the change in the health condition of the target subject indicates deterioration. Preferably, the output control unit performs control to output the prescription information.

Preferably, the obesity parameter and the bone parameter are calculated on the basis of a radiographic image obtained by performing radiography for the target subject using a stacked radiation detector.

Preferably, the obesity parameter is any one of weight, a body-fat percentage, or a body mass index and the bone parameter is any one of bone mass or bone density.

Preferably, the target subject is a pet.

According to the present disclosure, there is provided a method for operating a health management apparatus. The method comprises: an acquisition step of acquiring an obesity parameter indicating a degree of obesity of a target subject and a bone parameter indicating a degree of bone strength of the target subject; a first derivation step of deriving a health condition of the target subject on the basis of a correlation between the obesity parameter and the bone parameter; and an output control step of performing control to output the health condition.

According to the present disclosure, there is provided a program for operating a health management apparatus. The program causes a computer to function as: an acquisition unit that acquires an obesity parameter indicating a degree of obesity of a target subject and a bone parameter indicating a degree of bone strength of the target subject; a first derivation unit that derives a health condition of the target subject on the basis of a correlation between the obesity parameter and the bone parameter; and an output control unit that performs control to output the health condition.

According to the technology of the present disclosure, it is possible to provide a health management apparatus, a method for operating the health management apparatus, and a program for operating the health management apparatus which can notify health conditions referring to both an obesity parameter and a bone parameter.

BRIEF DESCRIPTION OF THE DRAWINGS

Exemplary embodiments according to the technique of the present disclosure will be described in detail based on the following figures, wherein:

FIG. 17 is a diagram illustrating a health condition change table;

FIG. 23 is a diagram illustrating a medical examination result display screen according to the third embodiment in which a change in the health conditions of a similar pet is not displayed;

FIG. 24 is a diagram illustrating a medical examination result display screen according to the third embodiment in which the change in the health conditions of the similar pet is displayed;

FIG. 30 is a diagram illustrating a medical examination result display screen according to the fourth embodiment in which the prescription information on the improved pet is displayed.

DESCRIPTION OF THE PREFERRED EMBODIMENTS

First Embodiment

Figure 1:
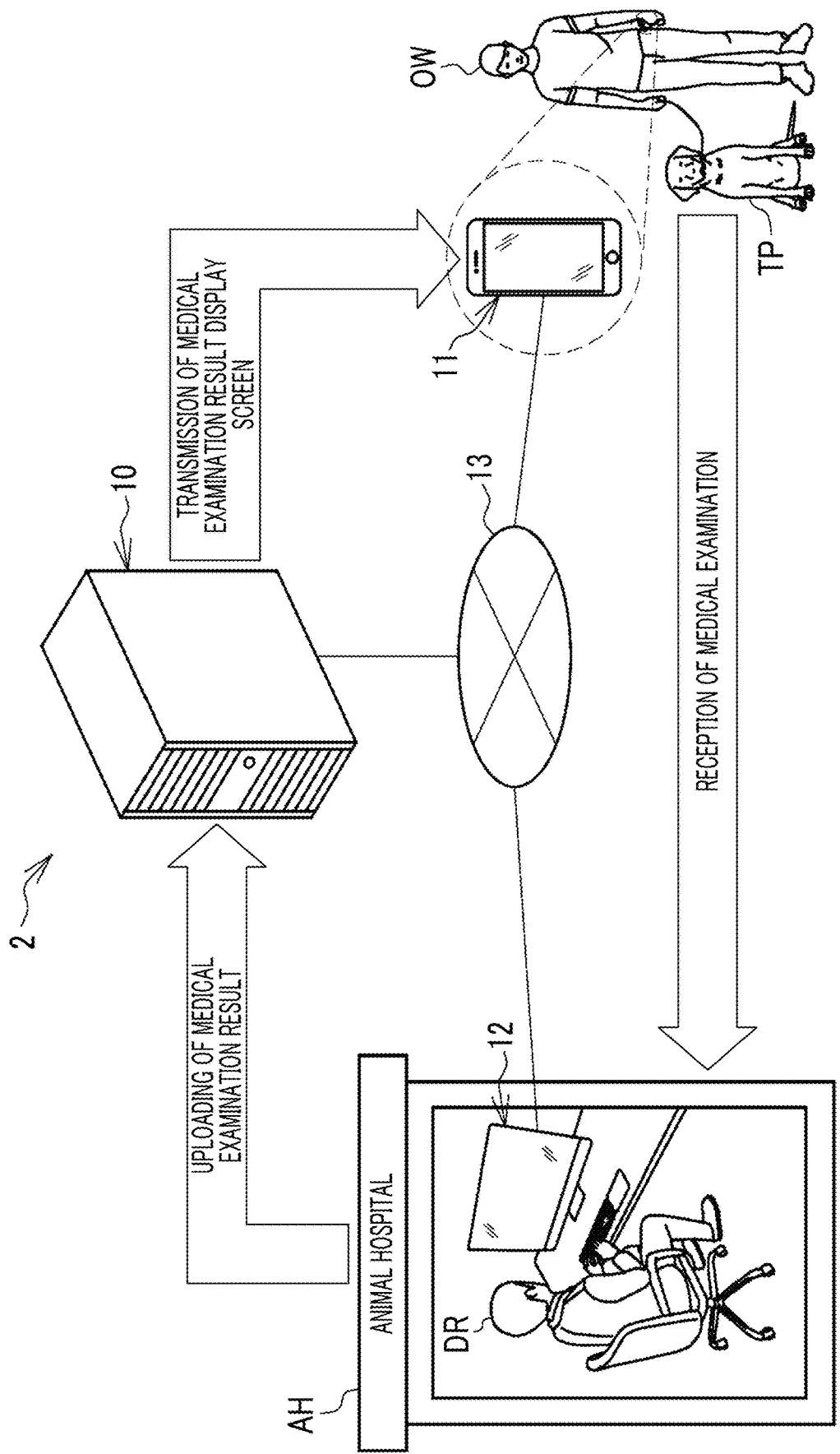
FIG. 1 is a diagram illustrating a health management system.

In FIG. 1, a health management system 2 is a system that manages a health condition of a target pet TP which is an example of a "target subject" according to the technology of the present disclosure. The health management system 2 comprises a health management apparatus 10, an owner terminal 11 that is owned by an owner OW of the target pet TP, and a hospital terminal 12 that is operated by, for example, a doctor DR in an animal hospital AH. The health management apparatus 10 is, for example, a server computer. The owner terminal 11 is, for example, a smart phone. The hospital terminal 12 is, for example, a desktop personal computer. In practice, there are a plurality of target pets TP, owners OW, and animal hospitals AH. Therefore, in practice, there are a plurality of owner terminals 11 and a plurality of hospital terminals 12.

The health management apparatus 10, the owner terminal 11, and the hospital terminal 12 are connected through a network 13 so as to communicate with each other. The network 13 is a wide area network (WAN) such as the Internet or a public telecommunication network.

The owner OW visits the animal hospital AH with the target pet TP such that the target pet TP receives a medical examination at the animal hospital AH. The doctor DR operates the hospital terminal 12 to upload the medical examination results MR (see FIG. 3) of the target pet TP to the health management apparatus 10.

The health management apparatus 10 transmits an upload notification indicating that the medical examination results MR have been uploaded from the hospital terminal 12 to the owner terminal 11. In a case in which the upload notification is received, the owner OW operates the owner terminal 11 to transmit a transmission request to the health management apparatus 10. The health management apparatus 10 receives the transmission request from the owner terminal 11 and transmits a medical examination result display screen 70 (see, for example, FIG. 11) on which the medical examination results MR have been displayed to the owner terminal 11.

Figure 2:
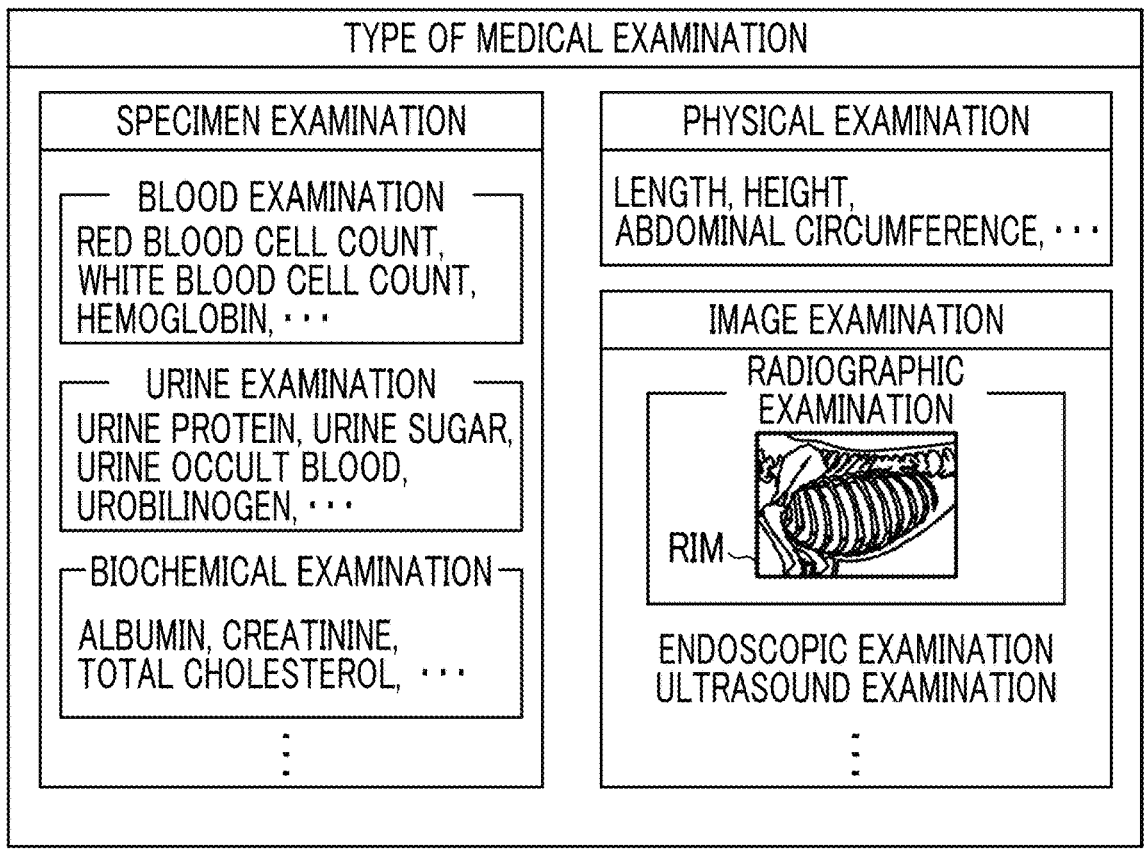
FIG. 2 is a diagram illustrating the type of medical examination.

In FIG. 2, the types of medical examinations are mainly divided into a specimen examination, a physical examination, and an image examination. Examples of the specimen examination include a blood examination, a urine examination, and a biochemical examination. The blood examination includes items, such as a red blood cell count, a white blood cell count, and hemoglobin. The urine examination includes items, such as urine protein, urine sugar, urine occult blood, and urobilinogen. The biochemical examination includes items, such as albumin, creatinine, and total cholesterol. The physical examination includes items, such as length, height, and abdominal circumference. The medical examination results MR of the specimen examination and the physical examination are the numerical values of the above-mentioned items. Examples of the image examination include a radiographic examination, an endoscopic examination, and an ultrasound examination. The medical examination results MR of the image examination are medical images such as radiographic images RIM in the radiographic examination.

Figure 3:
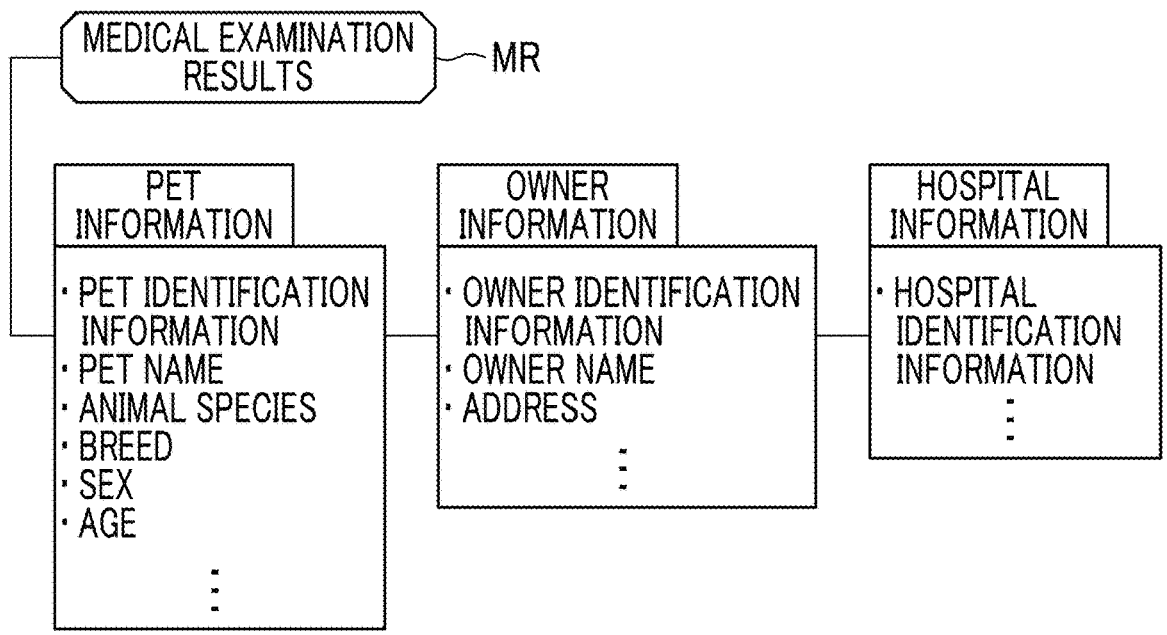
FIG. 3 is a diagram illustrating various kinds of information associated with medical examination results.

As illustrated in FIG. 3, pet information, owner information, and hospital information are associated with the medical examination results MR. The pet information includes, for example, pet identification information, a pet name, an animal species, a breed, sex, and age. The pet identification information is identification data (ID) including a symbol and/or a number. Examples of the animal species include a dog and a cat. In a case in which the target pet TP is a dog, the breed is, for example, Labrador Retriever or Shiba Inu. The owner information includes, for example, owner identification information, an owner name, and an address. The hospital information includes, for example, hospital identification information. The pet information, the owner information, and the hospital information are uploaded from the hospital terminal 12 to the health management apparatus 10 together with the medical examination results.

Figure 4:
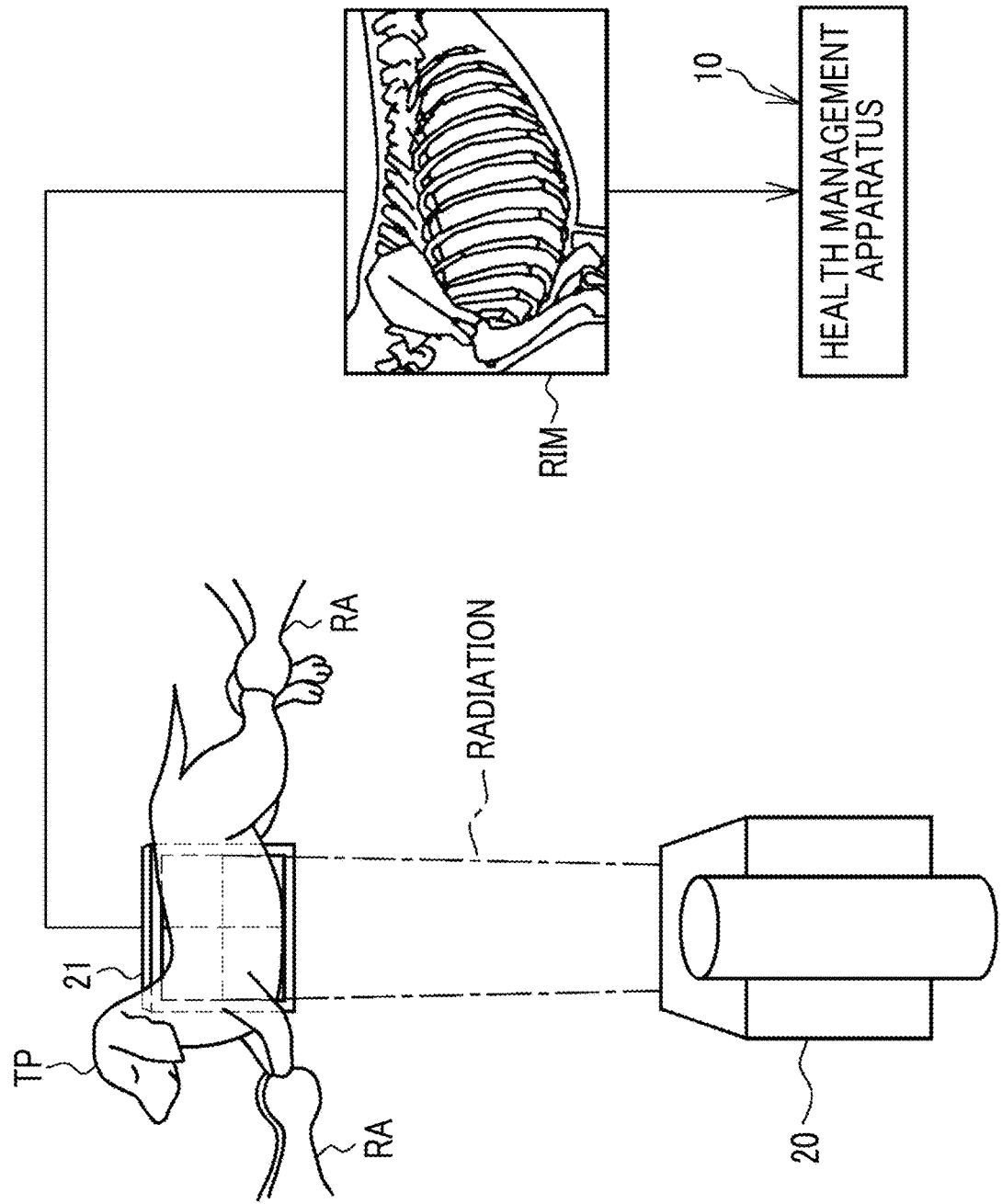
FIG. 4 is a diagram illustrating an aspect of a radiographic examination of a pet in an animal hospital.

In FIG. 4 illustrating an aspect of the radiographic examination of the target pet TP in the animal hospital AH, a radiation source 20 and a radiation detector 21 are used in the radiographic examination. The target pet TP is disposed between the radiation source 20 and the radiation detector 21. The radiation source 20 emits radiation to the target pet TP. The radiation detector 21 detects the radiation which has been emitted from the radiation source 20 and then transmitted through the target pet TP and outputs the radiographic image RIM. The radiation is, for example, X-rays or γ-rays.

In the radiographic examination, the target pet TP lies on its side on a bed (not illustrated) and the limbs are held by a radiology technician RA who performs the radiographic examination. Then, the radiation detector 21 is inserted under the target pet TP. In some cases, the radiographic examination may be performed with the target pet TP lying on its face or lying on its back on the bed. In addition, in some cases, the front legs and waist of the target pet TP are held by the radiology technician RA.

A portable radiation source, such as a product name "CALNEO Xair" (manufactured by FUJIFILM Corporation), may be used as the radiation source 20. In a case in which the portable radiation source is used, the target pet TP in the standing position may be irradiated with radiation to capture the radiographic image RIM, unlike the case in which the target pet TP lies on its side on the bed and the limbs of the target pet TP are held by the radiology technician RA as illustrated in FIG. 4. In a case in which the target pet TP lies on its side on the bed, there is a concern that the target pet TP will be exposed to radiation. Therefore, the radiology technician RA needs to hold, for example, the limbs of the target pet TP. In contrast, in a case in which the portable radiation source is used, the radiology technician RA does not need to hold, for example, the limbs of the target pet TP. Therefore, it is possible to capture the radiographic image RIM of the target pet TP in a more natural standing position.

Figure 5:
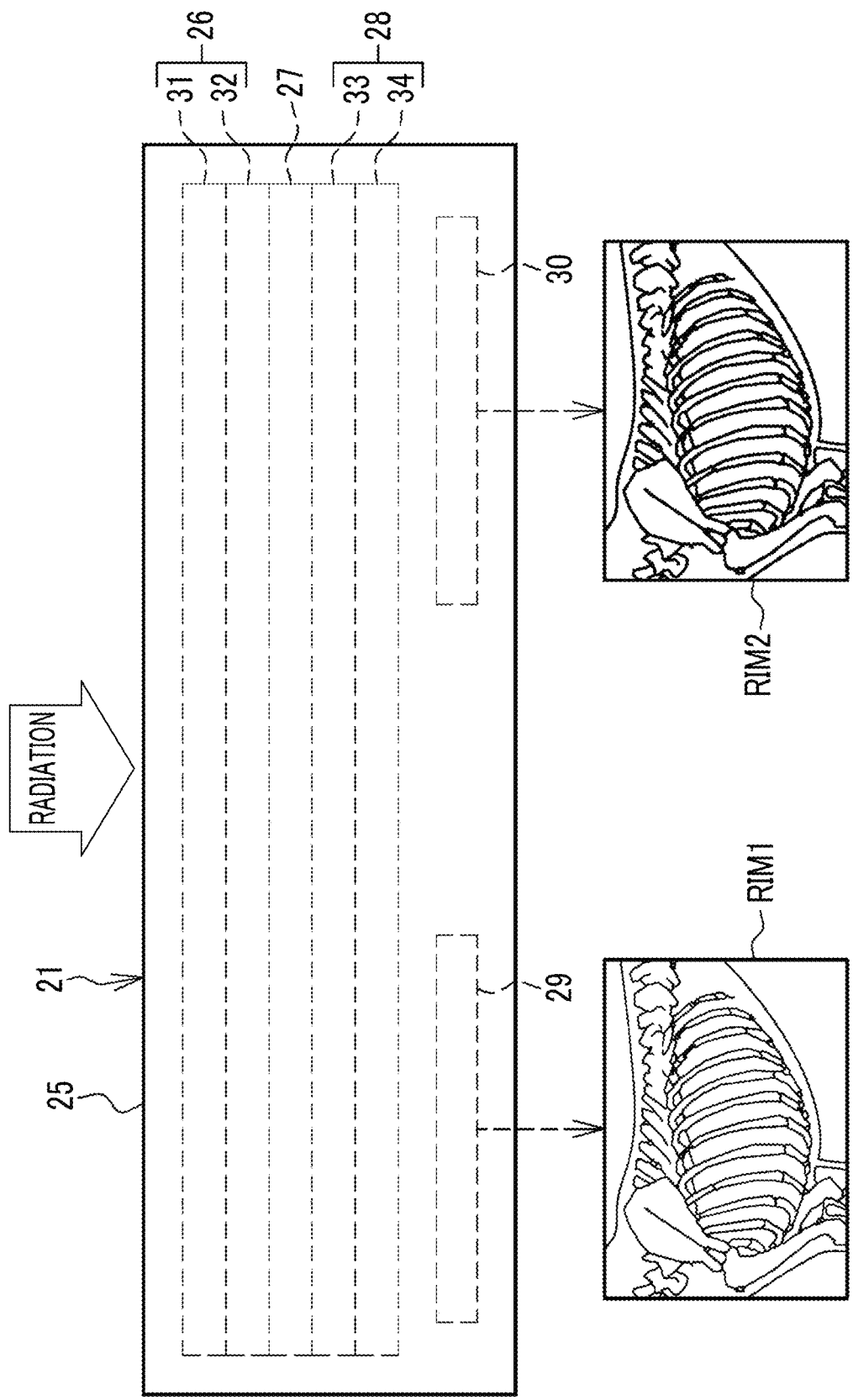
FIG. 5 is a diagram illustrating a radiation detector.

As illustrated in FIG. 5, the radiation detector 21 comprises a portable housing 25. The housing 25 includes, for example, a first radiation detection unit 26, a radiation limiting plate 27, a second radiation detection unit 28, a first circuit unit 29, and a second circuit unit 30. The first radiation detection unit 26, the radiation limiting plate 27, and the second radiation detection unit 28 are stacked in this order as viewed from the front side of the housing 25 on which radiation is incident. That is, the radiation detector 21 is an example of a "stacked radiation detector" according to the technology of the present disclosure. Specifically, the radiation detector 21 is, for example, a product name "CAL-NEO Dual" (manufactured by FUJIFILM Corporation).

The first radiation detection unit 26 includes a first light detection substrate 31 and a first scintillator 32. The second radiation detection unit 28 includes a second light detection substrate 33 and a second scintillator 34. The first light detection substrate 31 and the first scintillator 32 are stacked in this order as viewed from the front side of the housing 25. The second light detection substrate 33 and the second scintillator 34 are stacked in this order as viewed from the front side of the housing 25. The housing 25 also includes, for example, a battery that supplies power to each unit and a wireless communication unit that transmits the radiographic image RIM, which is not illustrated.

The first scintillator 32 and the second scintillator 34 have phosphors, convert incident radiation into visible light, and emit the visible light. The first scintillator 32 and the second scintillator 34 have different phosphors. The first scintillator 32 has, for example, CsI:Tl (thallium activated cesium iodide) as the phosphor. The second scintillator 34 has, for example, GOS ($Gd_2O_2S$:Tb, terbium-activated gadolinium oxysulfide) as the phosphor.

The first light detection substrate 31 and the second light detection substrate 33 detect the visible light emitted from the first scintillator 32 and the second scintillator 34 and convert the visible light into an electric signal, respectively. Specifically, the first light detection substrate 31 and the second light detection substrate 33 have a plurality of pixels which are arranged in a two-dimensional matrix. As is well known, the pixel includes a photoelectric conversion unit which receives incident visible light, generates charge (electron-hole pair), and accumulates the charge and a switching element such as a thin film transistor (TFT) which controls the accumulation of charge to the photoelectric conversion unit and the reading of charge from the photoelectric conversion unit.

The first circuit unit 29 controls the driving of, for example, the switching elements of the first light detection substrate 31 and generates a first radiographic image RIM1 on the basis of the electric signal output from the first light detection substrate 31. Similarly, the second circuit unit 30 controls the driving of, for example, the switching elements of the second light detection substrate 33 and generates a second radiographic image RIM2 on the basis of the electric signal output from the second light detection substrate 33. The first radiographic image RIM1 and the second radiographic image RIM2 are examples of a "radiographic image" according to the technology of the present disclosure. The first radiographic image RIM1 and the second radiographic image RIM2 are uploaded as the medical examination results MR to the health management apparatus 10. The first light detection substrate 31 and the first scintillator 32 may be stacked in the order of the first scintillator 32 and the first light detection substrate 31 as viewed from the front side of the housing 25. This holds for the second light detection substrate 33 and the second scintillator 34. Further, the radiation detector 21 may not be an indirect conversion type according to this example that converts the radiation converted into visible light by the first scintillator 32 and the second scintillator 34 into an electric signal, but may be a direct conversion type that directly converts radiation into an electric signal.

The radiation limiting plate 27 limits the amount of radiation which is transmitted through the first radiation detection unit 26 and is then emitted to the second radiation detection unit 28. The radiation limiting plate 27 is made of, for example, copper or tin. Since the radiation is absorbed by the radiation limiting plate 27 and the first radiation detection unit 26, the second radiation detection unit 28 is irradiated with a smaller amount of radiation than the first radiation detection unit 26. Further, the radiation limiting plate 27 absorbs a large number of low-energy components (also referred to as soft ray components) of the radiation. Therefore, the second radiation detection unit 28 is irradiated with radiation whose energy distribution is biased toward a high energy component (also referred to as a hard ray component). That is, according to the radiation detector 21, the same effect as that in a case in which two types of radiation having different energy distributions are emitted by one radiation emission operation is obtained.

The first radiographic image RIM1 and the second radiographic image RIM2 include both bone tissues, such as the ribs and the spine, and soft tissues, such as the lung and the stomach. However, the energy levels of radiation which are easily absorbed by the bone tissue and the soft tissue are different from each other. Therefore, the bone tissue included in the first radiographic image RIM1 and the bone tissue included in the second radiographic image RIM2 have different pixel values. Further, the soft tissue included in the first radiographic image RIM1 and the soft tissue included in the second radiographic image RIM2 also have different pixel values.

The apparatus that captures the first radiographic image RIM1 and the second radiographic image RIM2 may be a bone density measurement apparatus in which a radiation source, a radiation detector provided with one radiation detection unit, and a pedestal are integrated. In this case, since the radiation detector includes only one radiation detection unit, it is possible to acquire the first radiographic image RIM1 and the second radiographic image RIM2 by detecting radiation with the radiation detector whenever two types of radiation having different energy levels are emitted twice from the radiation source. Alternatively, any method, such as a quantitative computed tomography (QCT) method using a computed tomography (CT) apparatus, may be used as long as it can measure bone density using radiation.

Figure 6:
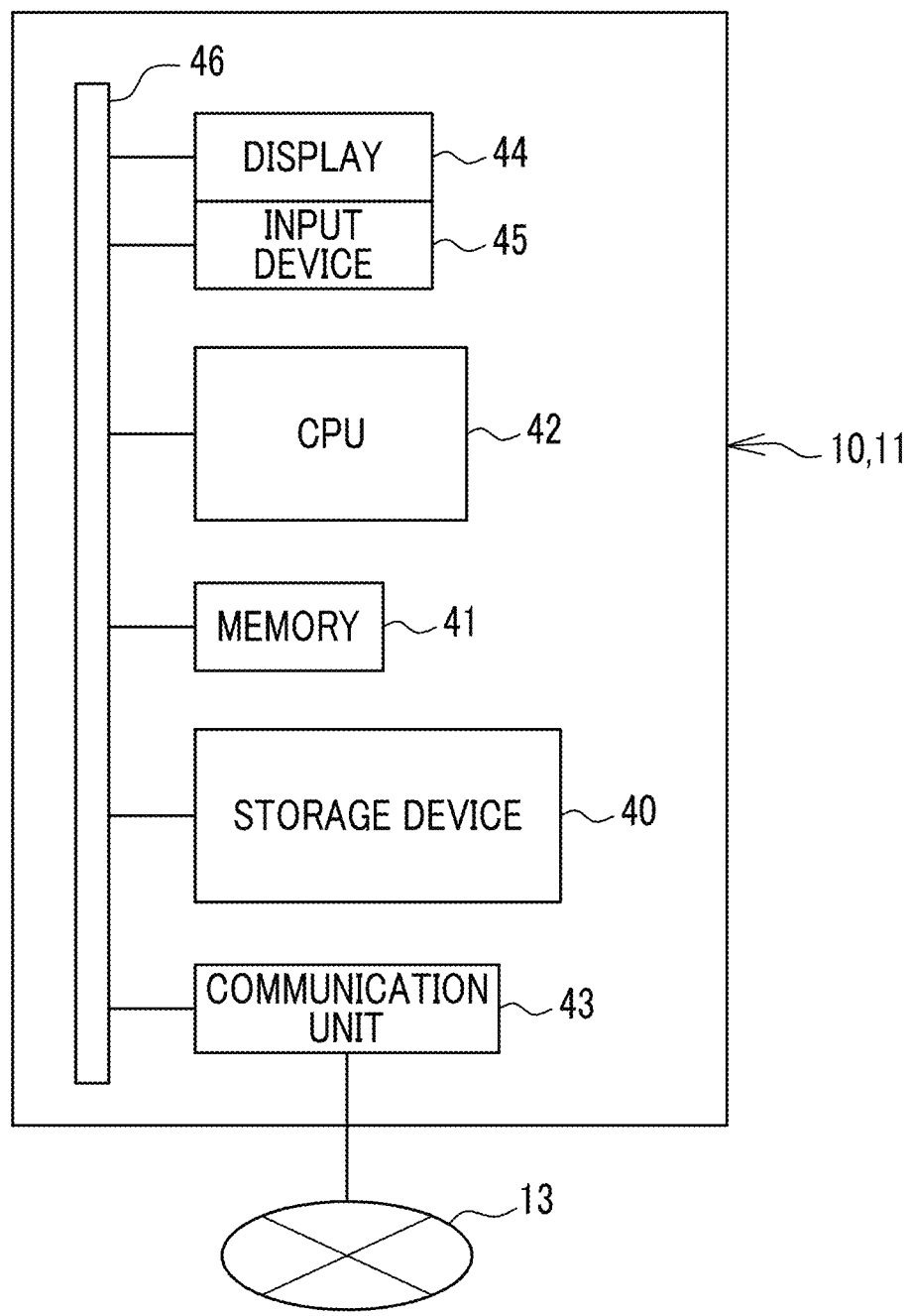
FIG. 6 is a block diagram illustrating a computer forming each of a health management apparatus and an owner terminal.

In FIG. 6, computers forming the health management apparatus 10 and the owner terminal 11 basically have the same configuration and comprise a storage device 40, a memory 41, a central processing unit (CPU) 42, a communication unit 43, a display 44, and an input device 45. These components are connected to each other through a bus line 46.

The storage device 40 is a hard disk drive that is provided in the computer forming each of the health management apparatus 10 and the owner terminal 11 or is connected to the computer through a cable or a network. Alternatively, the storage device 40 is a disk array in which a plurality of hard disk drives are connected in series to each other. The storage device 40 stores, for example, a control program, such as an operating system, or various application programs (hereinafter, abbreviated to APs) and various types of data associated with the programs.

The memory 41 is a work memory used by the CPU 42 to perform processes. The CPU 42 loads the program stored in the storage device 40 to the memory 41 and performs the process based on the program to control the overall operation of each unit of the computer.

The communication unit 43 is a network interface that controls the transmission of various kinds of information through the network 13. The display 44 displays various screens. The various screens have operation functions by a graphical user interface (GUI). The computers forming the health management apparatus 10 and the owner terminal 11 receive operation commands input from the input device 45 through various screens. The input device 45 is, for example, a keyboard, a mouse, or a touch panel.

In the following description, a suffix "A" is attached to each component of the computer forming the health management apparatus 10 and a suffix "B" is attached to each component of the computer forming the owner terminal 11 to distinguish the components.

Figure 7:
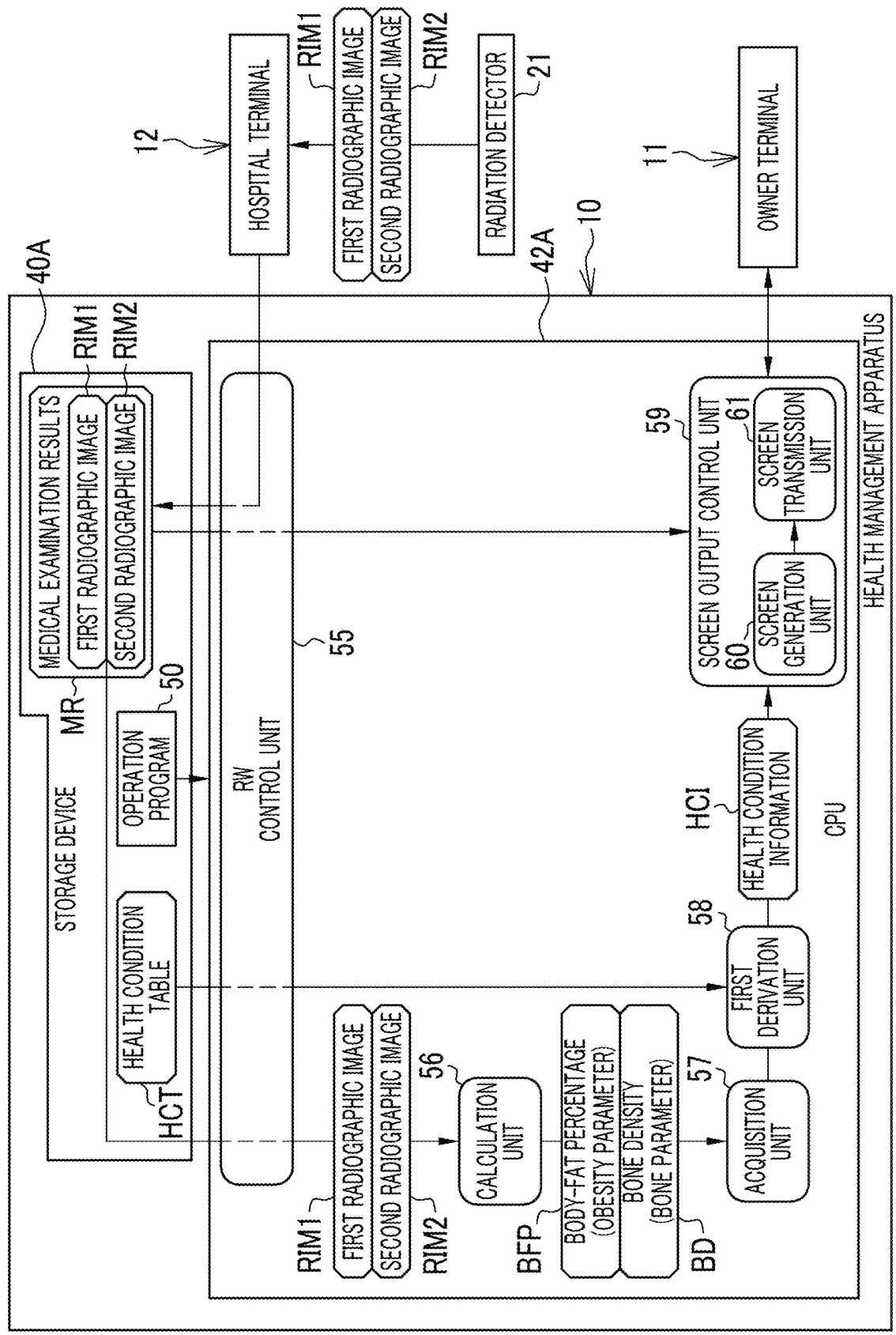
FIG. 7 is a block diagram illustrating a processing unit of a CPU of the health management apparatus.

In FIG. 7, a storage device 40A of the health management apparatus 10 stores an operation program 50. The storage device 40A stores the medical examination results MR and a health condition table HCT in addition to the operation program 50. That is, the storage device 40A is an example of a "storage unit" according to the technology of the present disclosure.

The operation program 50 is an example of a "program for operating a health management apparatus" according to the technology of the present disclosure. In a case in which the operation program 50 is run, a CPU 42A of the health management apparatus 10 functions as a read/write (hereinafter, abbreviated to RW) control unit 55, a calculation unit 56, an acquisition unit 57, a first derivation unit 58, and a screen output control unit 59 in cooperation with, for example, the memory 41. The screen output control unit 59 includes a screen generation unit 60 and a screen transmission unit 61. The concept of the "screen output control unit 59" described below includes the screen generation unit 60 and the screen transmission unit 61.

The RW control unit 55 controls the reading of various kinds of data in the storage device 40A and the storage of various kinds of data to the storage device 40A. The RW control unit 55 stores the medical examination results MR (including pet information, owner information, and hospital information) from the hospital terminal 12 in the storage device 40A. The medical examination results MR include the first radiographic image RIM1 and the second radiographic image RIM2 from the radiation detector 21. The RW control unit 55 reads the medical examination results MR from the storage device 40A. Then, the RW control unit 55 outputs the first radiographic image RIM1 and the second radiographic image RIM2 included in the read medical examination results MR to the calculation unit 56 and outputs the medical examination results MR to the screen output control unit 59.

The RW control unit 55 reads the health condition table HCT from the storage device 40A and outputs the read health condition table HCT to the first derivation unit 58. That is, the RW control unit 55 is an example of a "reading unit" according to the technology of the present disclosure.

The calculation unit 56 calculates a body-fat percentage BFP which is an example of an obesity parameter indicating the degree of obesity of the target pet TP and bone density BD which is an example of a bone parameter indicating the degree of bone strength of the target pet TP on the basis of the first radiographic image RIM1 and the second radiographic image RIM2. The calculation unit 56 calculates the body-fat percentage BFP of the target pet TP from the first radiographic image RIM1 and the second radiographic image RIM2 using, for example, the method described in JP2015-038734A. In addition, the calculation unit 56 calculates the bone density BD of the target pet TP using, for example, the dual-energy X-ray absorptiometry (DXA) method described in JP2018-192056A. The calculation unit 56 outputs the calculated body-fat percentage BFP and bone density BD to the acquisition unit 57.

The acquisition unit 57 acquires the body-fat percentage BFP and the bone density BD from the calculation unit 56. The acquisition unit 57 outputs the body-fat percentage BFP and the bone density BD to the first derivation unit 58.

The first derivation unit 58 derives the health conditions of the target pet TP on the basis of the correlation between the health condition table HCT from the RW control unit 55 and the body-fat percentage BFP and the bone density BD from the acquisition unit 57. The first derivation unit 58 creates health condition information HCI indicating the derivation results of the health conditions. The first derivation unit 58 outputs the health condition information HCI to the screen output control unit 59.

The screen output control unit 59 receives a request to transmit various screens including the medical examination result display screen 70 from the owner terminal 11. In a case in which the transmission request is received, the screen output control unit 59 controls the output of various screens to the owner terminal 11. Specifically, the screen output control unit 59 outputs various screens in the form of screen data for web transmission created by a markup language, such as Extensible Markup Language (XML). Then, it is possible to browse various screens on a web browser with the owner terminal 11. Other data description languages including Javascript (registered trademark) Object Notation (JSON) may be used instead of XML.

The screen generation unit 60 generates screen data of various screens and outputs the generated screen data to the screen transmission unit 61. The screen transmission unit 61 transmits the screen data from the screen generation unit 60 to the owner terminal 11 which is the source of the request to transmit various screens.

Figure 8:
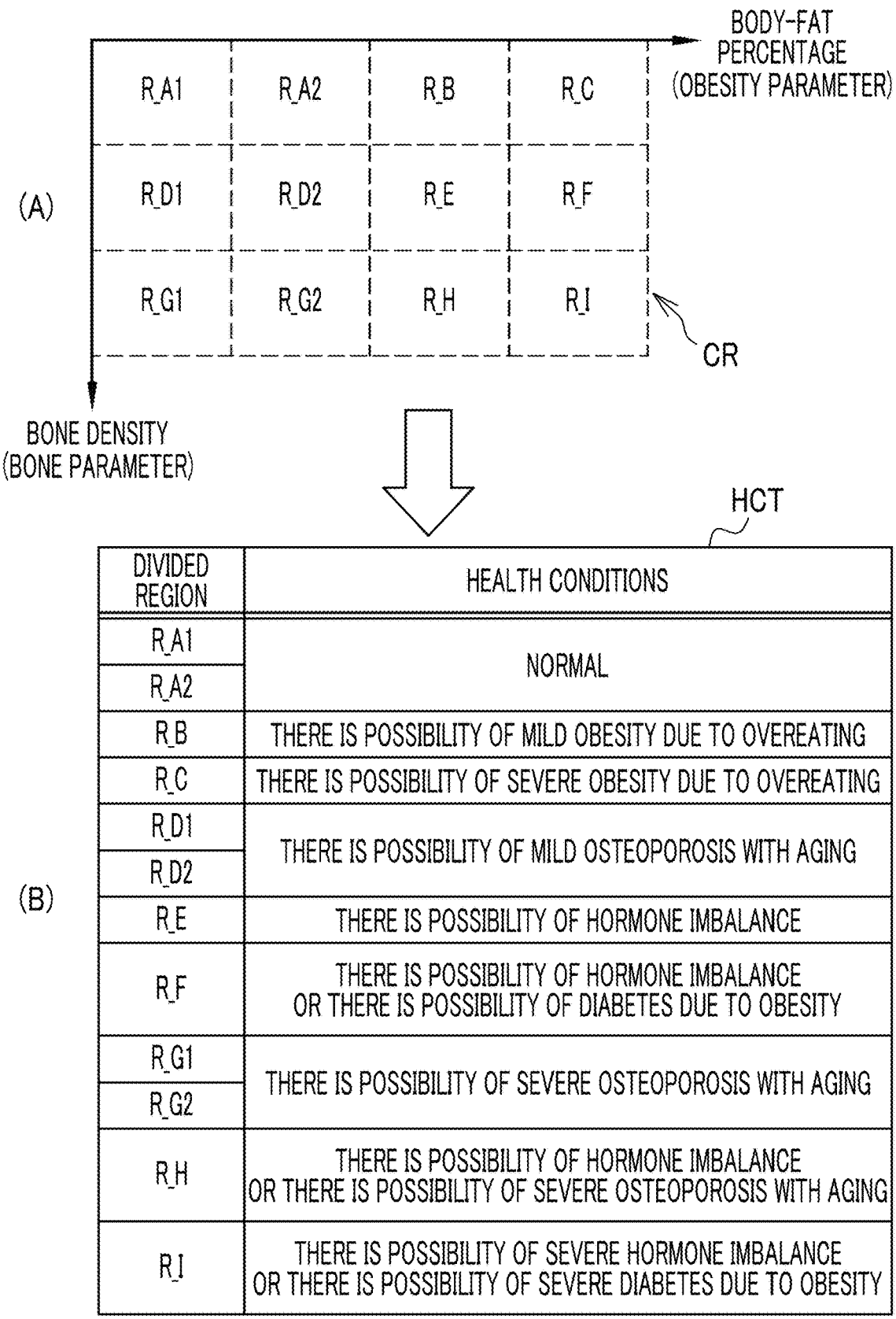
FIG. 8 is a diagram illustrating the formation of a health condition table. (A) of FIG. 8 illustrates a coordinate region which is a creation source of the health condition table and (B) of FIG. 8 illustrates the health condition table.

(A) of FIG. 8 illustrates a coordinate region CR which is the creation source of the health condition table HCT. The coordinate region CR is a region in which the body-fat percentage BFP is disposed on the horizontal axis and the bone density BD is disposed on the vertical axis. That is, the horizontal axis is an example of "one axis" according to the technology of the present disclosure and the vertical axis is an example of "the other axis" according to the technology of the present disclosure. The coordinate region CR is divided into a total of 12 divided regions R, that is, divided regions R_A1, R_A2, R_B, R_C, R_D1, R_D2, R_E, R_F, R_G1, R_G2, R_H, and R_I.

As illustrated in (B) of FIG. 8, the health condition table HCT is a table in which health conditions corresponding to each of the divided regions R_A1, R_A2, . . . of the coordinate region CR are registered. For example, "normal" is registered as the health condition in the divided regions R_A1 and R_A2 and "there is a possibility of mild obesity due to overeating" is registered as the health condition in the divided region R_B. In addition, for example, "there is a possibility of hormone imbalance or a possibility of diabetes due to obesity" is registered as the health condition in the divided region R_F.

Figure 9:
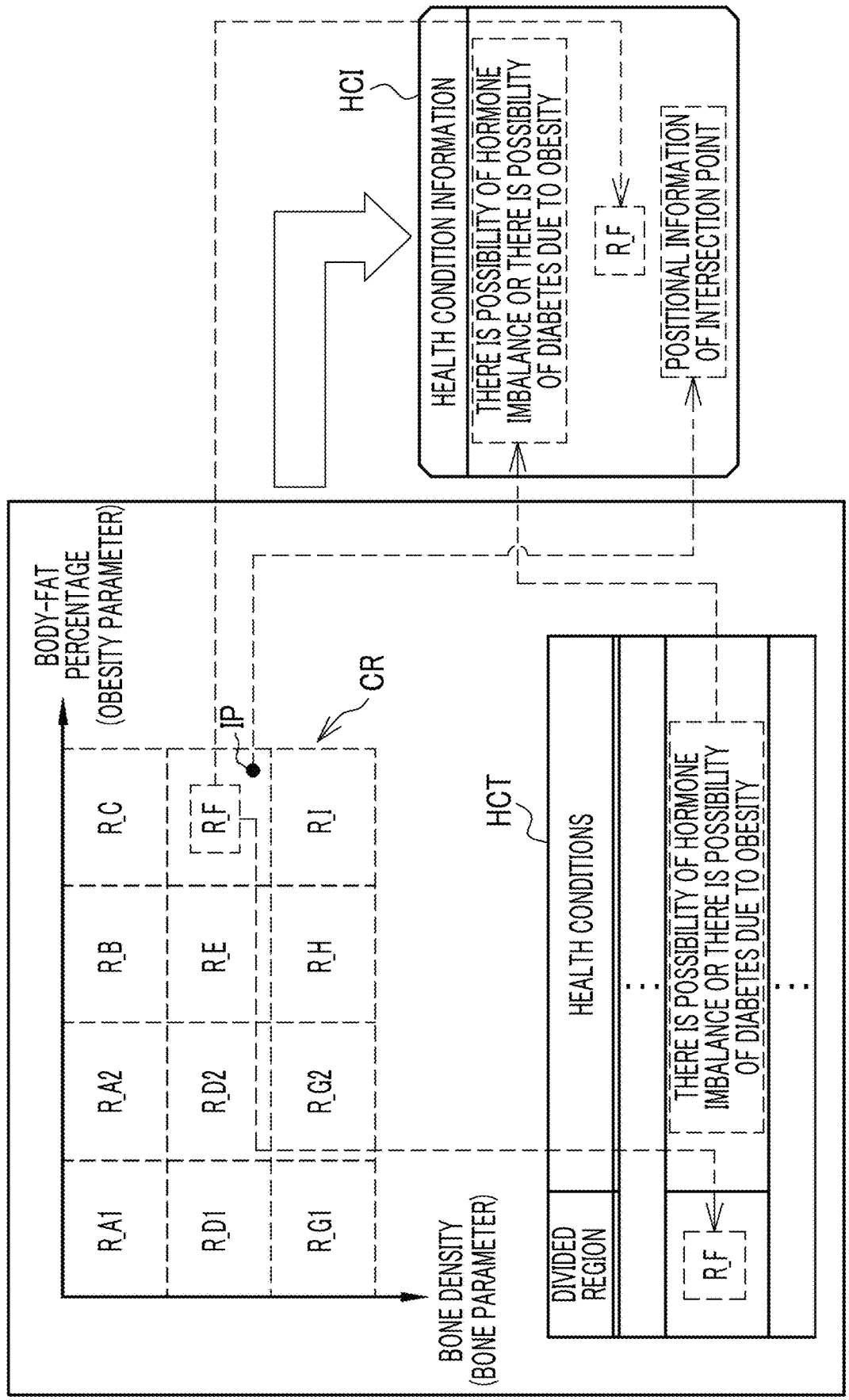
FIG. 9 is a diagram illustrating an aspect in which a first derivation unit derives the health conditions of a target pet.

As illustrated in FIG. 9, the first derivation unit 58 derives a health condition corresponding to the divided region R in which an intersection point IP of the body-fat percentage BFP and the bone density BD of the target pet TP is present from the health condition table HCT. The first derivation unit 58 creates the health condition information HCI including the derived health condition, the divided region R corresponding to and the derived health condition, and the positional information of the intersection point IP in the coordinate region CR indicated by the body-fat percentage BFP and the bone density BD. FIG. 9 illustrates an example in which the intersection point IP is present in the divided region R_F and "there is a possibility of hormone imbalance or there is a possibility of diabetes due to obesity" that is the health condition corresponding to the divided region R_F is derived.

Figure 10:
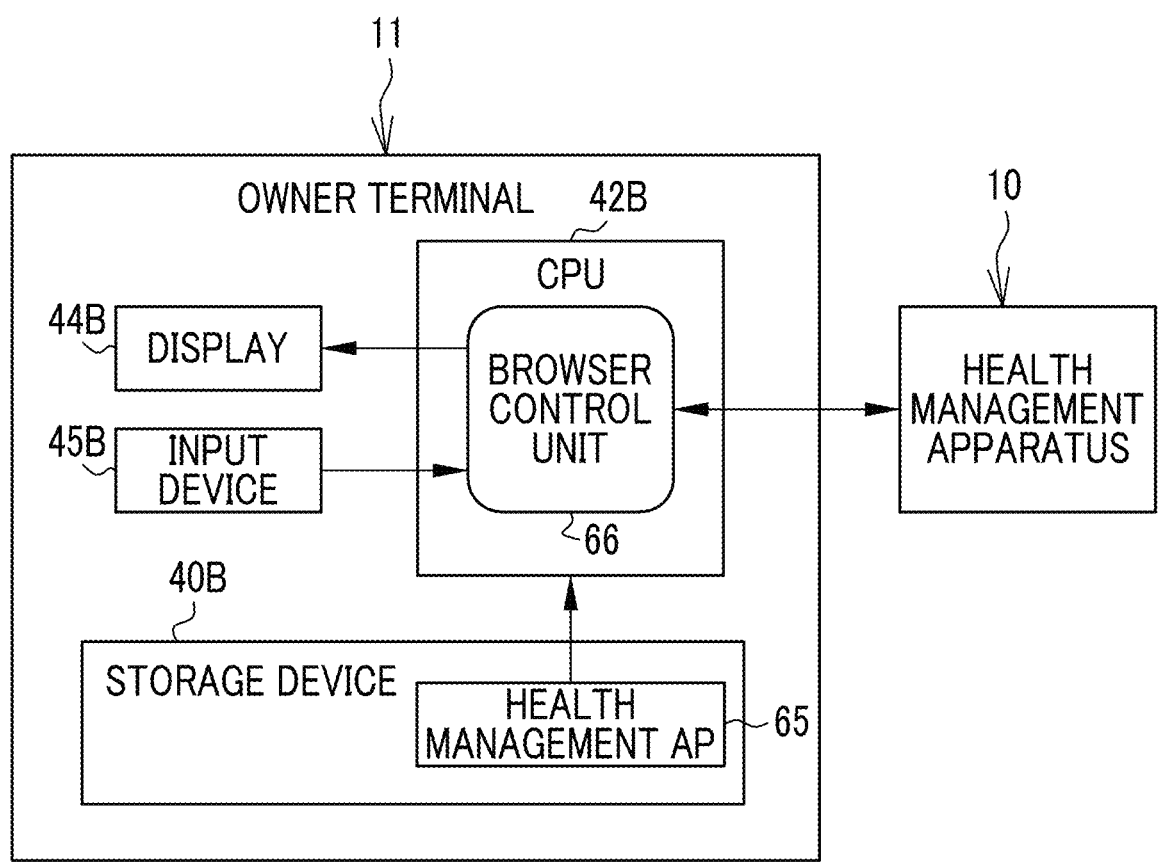
FIG. 10 is a block diagram illustrating a processing unit of a CPU of the owner terminal.

In FIG. 10, a health management AP 65 is stored in a storage device 40B of the owner terminal 11. In a case in which the health management AP 65 is executed and a web browser is started, a CPU 42B of the owner terminal 11 functions as a browser control unit 66 in cooperation with, for example, the memory 41. The browser control unit 66 controls the operation of the web browser. The browser control unit 66 receives screen data of various screens from the health management apparatus 10. The browser control unit 66 reproduces various screens displayed on the web browser on the basis of the screen data and displays the various screens on a display 44B.

In addition, the browser control unit 66 receives various operation commands input from an input device 45B by the owner OW through various screens. The operation commands include, for example, a command to access the health management apparatus 10 and a command to transmit various screens. The browser control unit 66 issues a request corresponding to the operation command to the health management apparatus 10. For example, the browser control unit 66 issues a request to transmit various screens to the health management apparatus 10 in response to a command to transmit various screens. Since the owner terminal 11 is a smart phone, the input device 45B is a touch panel.

Figure 11:
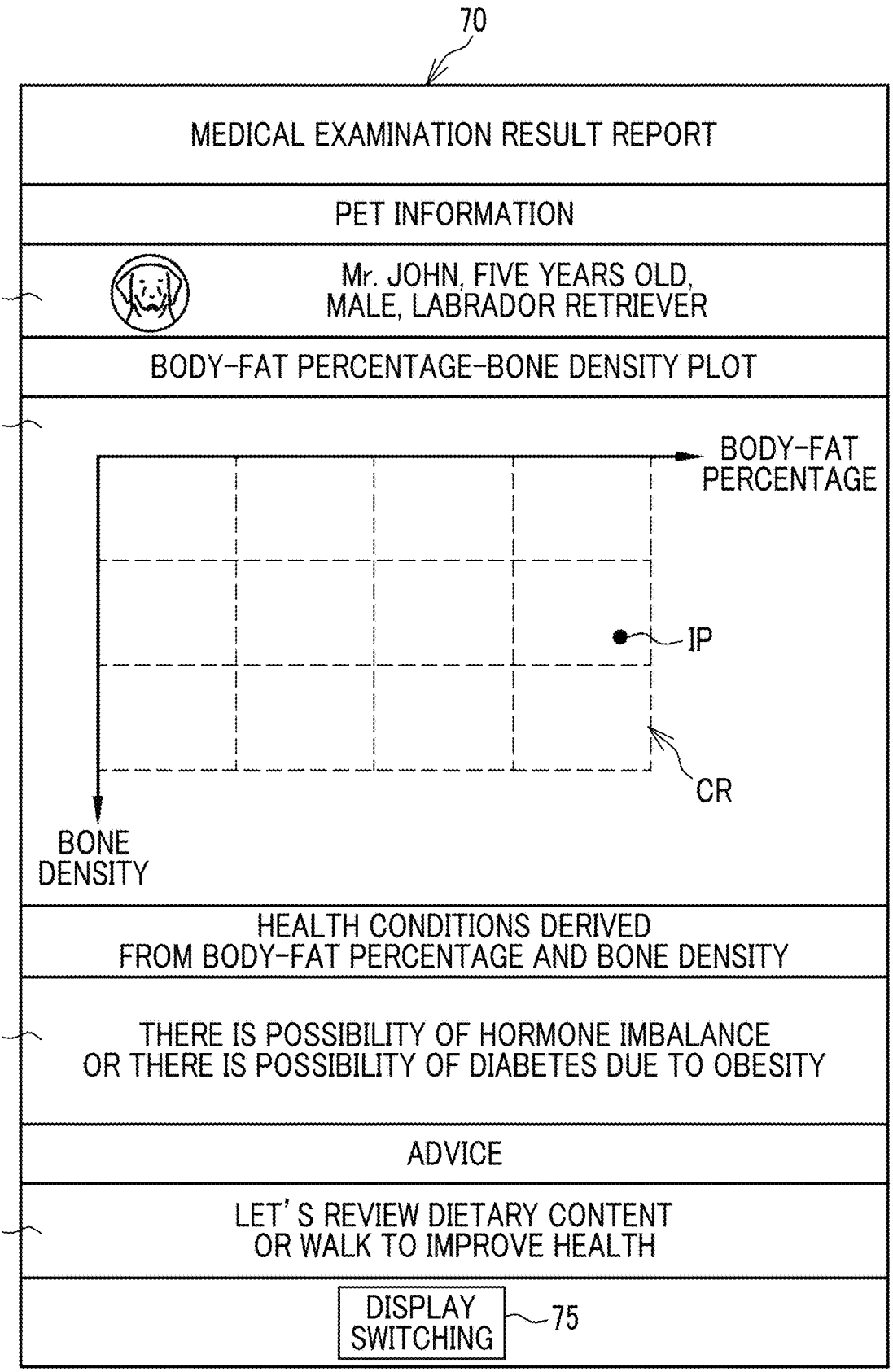
FIG. 11 is a diagram illustrating a medical examination result display screen.

In FIG. 11, the medical examination result display screen 70 displayed on the display 44B of the owner terminal 11 has a pet information display section 71, a coordinate region display section 72, a health condition display section 73, and an advice display section 74. In the pet information display section 71, a pet name, age, sex, and a breed are displayed together with a face photograph of the target pet TP. In the coordinate region display section 72, the coordinate region CR including the intersection point IP of the body-fat percentage BFP and the bone density BD of the target pet TP is displayed. In the health condition display section 73, the health conditions of the target pet TP derived by the first derivation unit 58 are displayed. In the advice display section 74, advice on the owner OW is displayed. That is, the screen output control unit 59 is an example of an "output control unit" according to the technology of the present disclosure.

A display switching button 75 is a button for switching the display content of the medical examination result display screen 70. Examples of the content displayed on the medical examination result display screen 70 include a list of the numerical values of each item of the specimen examination, a list of the numerical values of each item of the physical examination, and medical images, such as the radiographic images RIM, in addition to the health conditions referring to both the body-fat percentage BFP and the bone density BD illustrated in FIG. 11. In addition, a screen on which all of the medical examination results are comprehensively illustrated in a list form may be displayed. Further, a screen on which advice, such as a recommended walk distance and time or a recommended meal amount, is specifically illustrated may be displayed. Furthermore, a map screen showing a recommended walking course or a recommended pet food purchase screen may be displayed in response to the operation of the owner OW.

Figure 12:
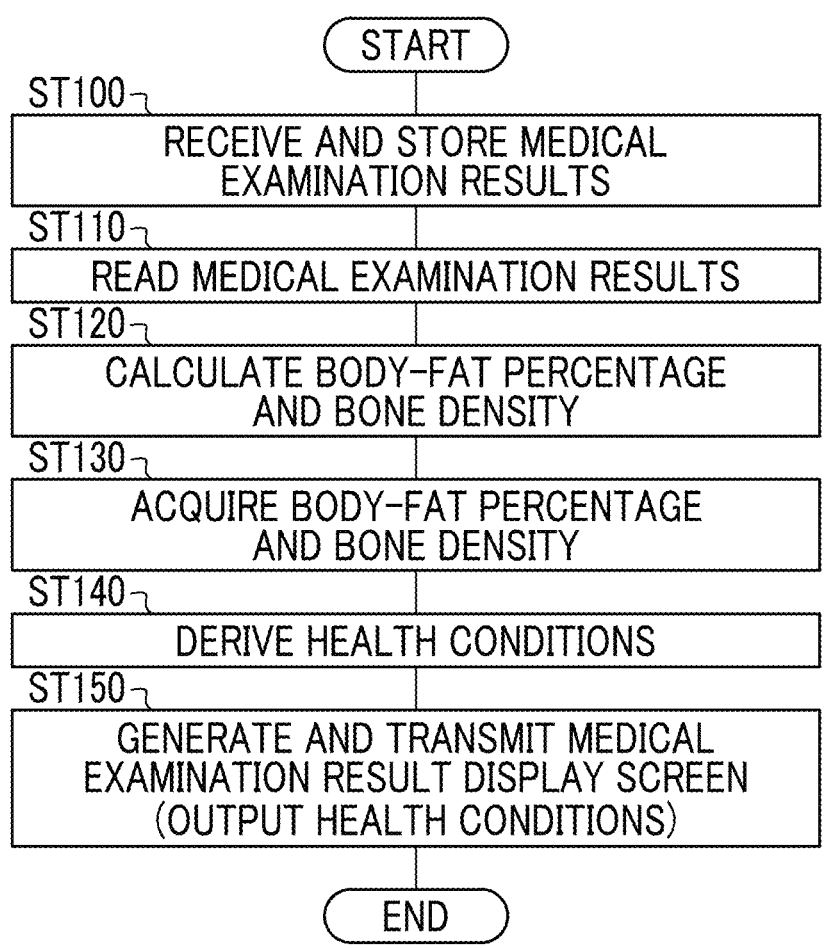
FIG. 12 is a flowchart illustrating a processing procedure of the health management apparatus.

Next, the operation of the above-mentioned configuration will be described with reference to a flowchart illustrated in FIG. 12. First, in a case in which the operation program 50 is run, as illustrated in FIG. 7, the CPU 42A of the health management apparatus 10 functions as the RW control unit 55, the calculation unit 56, the acquisition unit 57, the first derivation unit 58, and the screen output control unit 59 (the screen generation unit 60 and the screen transmission unit 61).

The medical examination results MR of the target pet TP are uploaded from the hospital terminal 12 of the animal hospital AH to the health management apparatus 10. The medical examination results MR are received by the RW control unit 55 and are then stored in the storage device 40A by the RW control unit 55 (Step ST100).

The medical examination results MR are read from the storage device 40A by the RW control unit 55 (Step ST110). The first radiographic image RIM1 and the second radiographic image RIM2 included in the medical examination results MR are output from the RW control unit 55 to the calculation unit 56. The calculation unit 56 calculates the body-fat percentage BFP (obesity parameter) and the bone density BD (bone parameter) of the target pet TP on the basis of the first radiographic image RIM1 and the second radiographic image RIM2 (Step ST120).

The body-fat percentage BFP and the bone density BD are output from the calculation unit 56 to the acquisition unit 57. Then, the acquisition unit 57 acquires the body-fat percentage BFP and the bone density BD (Step ST130). The body-fat percentage BFP and the bone density BD are output from the acquisition unit 57 to the first derivation unit 58. Step ST130 is an example of an "acquisition step" according to the technology of the present disclosure.

The health condition table HCT illustrated in FIG. 8 is input from the RW control unit 55 to the first derivation unit 58. Then, as illustrated in FIG. 9, the first derivation unit 58 derives a health condition corresponding to the divided region R in which the intersection point IP of the body-fat percentage BFP and the bone density BD of the target pet TP is present from the health condition table HCT (Step ST140). The first derivation unit 58 creates the health condition information HCI indicating the derivation result of the health condition. The health condition information HCI is output from the first derivation unit 58 to the screen output control unit 59. Step ST140 is an example of a "first derivation step" according to the technology of the present disclosure.

The screen output control unit 59 receives a request to transmit the medical examination result display screen 70 from the owner terminal 11. In a case in which the transmission request is received, the screen generation unit 60 of the screen output control unit 59 generates screen data of the medical examination result display screen 70 including, for example, the coordinate region display section 72 and the health condition display section 73 illustrated in FIG. 11. The screen data of the medical examination result display screen 70 is output to the screen transmission unit 61. The screen transmission unit 61 transmits the screen data of the medical examination result display screen 70 to the owner terminal 11 which is the request source of the transmission request (Step ST150). Step ST150 is an example of an "output control step" according to the technology of the present disclosure.

In the owner terminal 11, the browser control unit 66 displays the medical examination result display screen 70 from the health management apparatus 10 on the display 44B. The owner OW views the medical examination result display screen 70 and checks the medical examination results of the target pet TP.

As described above, the health management apparatus 10 comprises the acquisition unit 57, the first derivation unit 58, and the screen output control unit 59. The acquisition unit 57 acquires the body-fat percentage BFP and the bone density BD of the target pet TP. The first derivation unit 58 derives the health conditions of the target pet TP on the basis of the correlation between the body-fat percentage BFP and the bone density BD. The screen output control unit 59 performs control to output the health conditions of the target pet TP through the medical examination result display screen 70. Therefore, it is possible to know the health conditions referring to both the obesity parameter and the bone parameter. It is possible to respond to a demand for knowing the health conditions referring to both the obesity parameter and the bone parameter which are important parameters in determining the health conditions of the target pet TP.

Obesity results from only overeating or only the lack of exercise. The obesity causes diabetes and osteoporosis may develop with the progress of diabetes. In addition, osteoporosis is caused by only aging. As described above, since obesity and osteoporosis occur due to various factors, it is necessary to determine what causes the current health conditions from the correlation between the obesity parameter and the bone parameter and to propose, for example, diet, exercise, and medicines for improvement.

Many pets undergo castration surgery within about one year after birth. This makes the temperament of the pet gentle and suppresses problematic behaviors that are likely to develop during estrus. However, there is a concern that hormone secretion will decrease and bone will be brittle from a young age as adverse effects. In addition, it is also known that hormone imbalance tends to cause obesity and there is a concern that obesity will develop into diseases such as diabetes. However, even in a case in which the pet undergoing castration surgery has become obese, the cause of the obesity is not limited to the hormone imbalance caused by castration surgery and it is necessary to consider the simple case of overeating as the cause. Therefore, it is necessary to comprehensively determine what causes the current health conditions and to respond to the current health conditions on the basis of the results of the determination. The technology of the present disclosure is effective since it can be helpful in determining what causes the current health conditions.

The first derivation unit 58 derives the health conditions of the target pet TP using the health condition table HCT. Specifically, in the health condition table HCT, the health conditions corresponding to each of a plurality of divided regions R obtained by dividing the coordinate region CR in which the body-fat percentage BFP is disposed on the horizontal axis and the bone density BD is disposed on the vertical axis are registered. Then, the first derivation unit 58 derives a health condition corresponding to the divided region R in which the intersection point IP of the body-fat percentage BFP and the bone density BD of the target pet TP is present from the health condition table HCT. Therefore, it is possible to very simply derive the health condition of the target pet TP.

The screen output control unit 59 performs control to output the coordinate region CR in which the intersection point IP of the body-fat percentage BFP and the bone density BD of the target pet TP is present through the coordinate region display section 72 of the medical examination result display screen 70. Therefore, it is possible to easily recognize the correlation between the body-fat percentage BFP and the bone density BD.

The body-fat percentage BFP and the bone density BD are calculated on the basis of the first radiographic image RIM1 and the second radiographic image RIM2 obtained by performing radiography for the target pet TP using the radiation detector 21 in which the first radiation detection unit 26 and the second radiation detection unit 28 are stacked. Therefore, the body-fat percentage BFP and the bone density BD can be derived by one radiography operation. In a case in which the target pet TP is a long-haired breed, the appearance of the body is hidden by the hair and it is difficult to recognize obesity. However, the use of the first radiographic image RIM1 and the second radiographic image RIM2 makes it possible to exclude the influence of the hair and to find the hidden obesity.

In a case in which radiography is performed for the target pet TP as illustrated in FIG. 4, the target pet TP is held by the radiology technician RA. In a case in which not the radiation detector 21 but a radiation detector comprising only one radiation detection unit is used, it is necessary to emit two types of radiation with different energy distributions at different timings. Since two types of radiation with different energy distributions are emitted at different timings, at least several tens of seconds are required. In a case in which the subject is a human, the subject can remain stationary without moving for about several tens of seconds. However, in the case of the target pet TP, since the target pet TP is forced to take a different posture against the pet's will, the target pet TP is likely to move violently. Therefore, blurring is likely to occur in the first radiographic image RIM1 and the second radiographic image RIM2 due to the body motion of the target pet TP and the probability of imaging failure increases. In a case in which the imaging fails, re-imaging needs to be repeated until the imaging succeeds and the burden on both the target pet TP and the radiology technician RA increases. In a case in which the target pet TP has osteoporosis and is pressed with a strong force so as not to move, the risk of fracture increases. Therefore, the effect of calculating the body-fat percentage BFP and the bone density BD using one radiography operation is particularly effective in a case in which the subject is the target pet TP.

In addition, the animal hospital AH does not need to introduce a dedicated DXA apparatus and simply replaces the radiation detector used so far with the radiation detector 21. Therefore, it is possible to minimize equipment investment costs and to save an installation space.

As described above, the pet is likely to become obese due to the influence of castration surgery and tend to have brittle bones. That is, the pet has a high risk of obesity and osteoporosis at the same time regardless of age. Therefore, it is particularly meaningful to notify the health conditions referring to both the obesity parameter and the bone parameter in a case in which the subject is a pet.

Figure 13:
FIG. 13 is a diagram illustrating a medical examination result display screen in a case in which an obesity parameter is weight and a bone parameter is bone mass.
Figure 14:
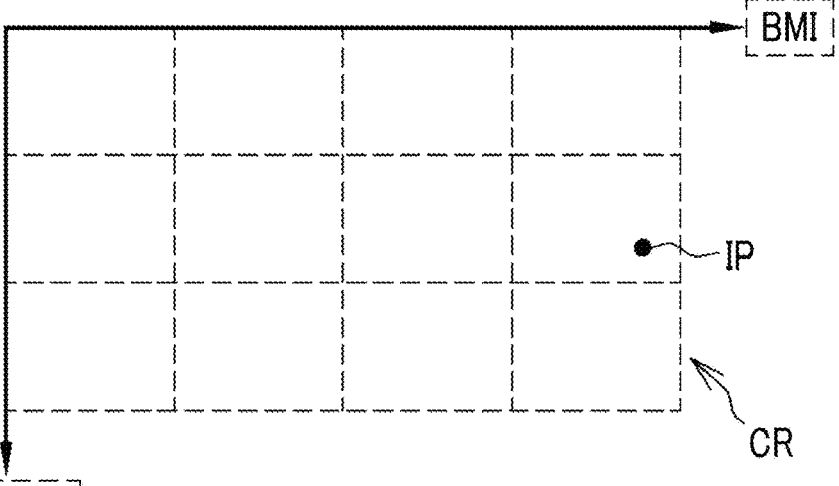
FIG. 14 is a diagram illustrating a medical examination result display screen in a case in which the obesity parameter is a body mass index and the bone parameter is bone mass.

As illustrated in the medical examination result display screen 70 of FIGS. 13 and 14, the bone parameter may be bone mass instead of the bone density BD. In addition, the obesity parameter may be weight (see FIG. 13) or a body mass index (BMI) (see FIG. 14) instead of the body-fat percentage BFP. In this case, the obesity parameter and the bone parameter may not be calculated on the basis of the first radiographic image RIM1 and the second radiographic image RIM2 obtained by performing radiography for the target pet TP using the radiation detector 21.

A coordinate region CR in which the bone parameter is disposed on the horizontal axis and the obesity parameter is disposed on the vertical axis may be used.

Second Embodiment

In a second embodiment illustrated in FIGS. 15 to 20, a change in the health condition of the target pet TP is derived and the derived change in the health condition is output.

Figure 15:
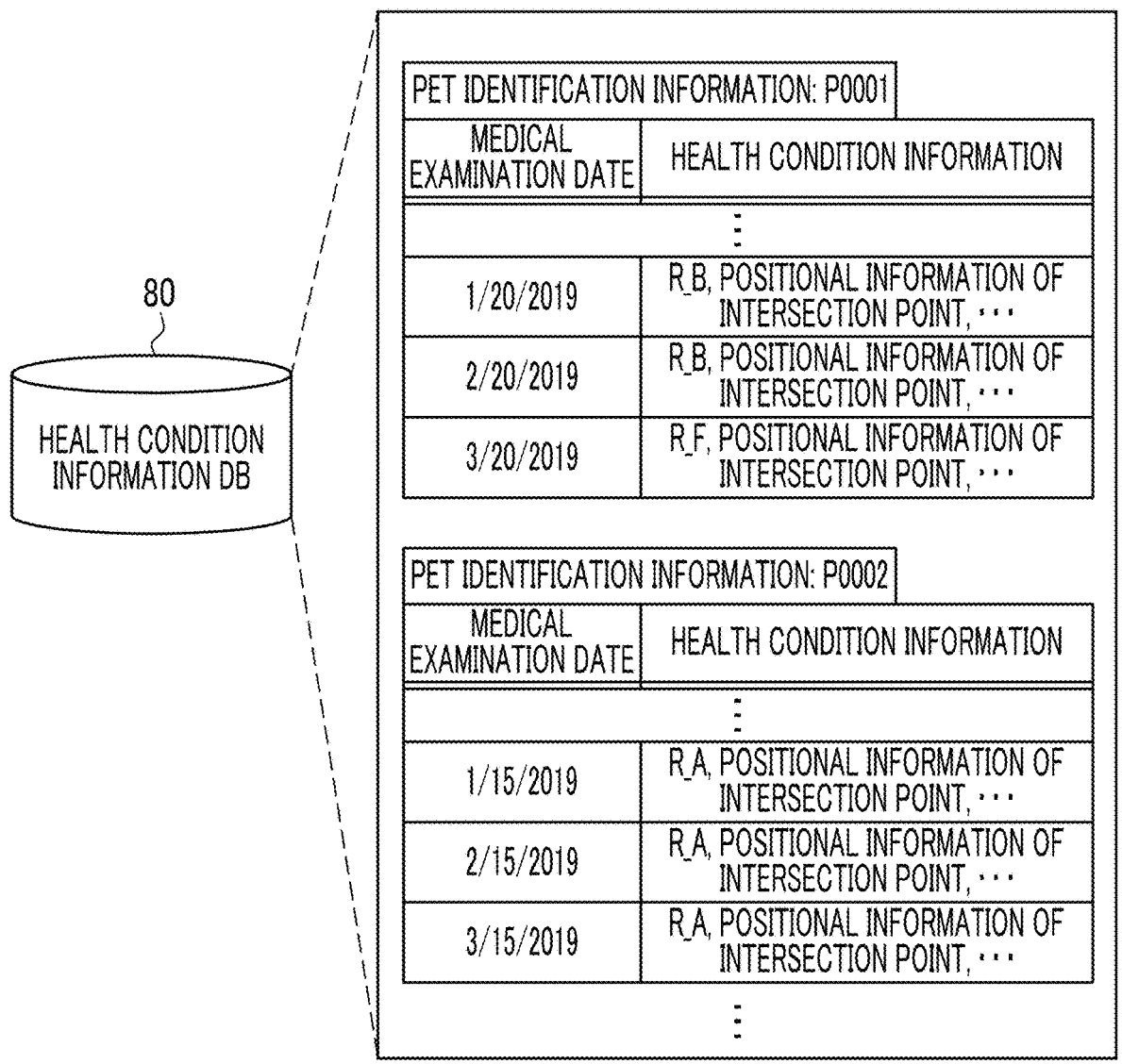
FIG. 15 is a diagram illustrating a health condition information DB.

In FIG. 15, a health condition information database (hereinafter, abbreviated to DB) 80 is stored in a storage device 40A of a health management apparatus according to the second embodiment. In the health condition information DB 80, a set of a medical examination date and the health condition information HCI is registered for each pet identification information item. As illustrated in FIG. 9, the health condition information HCI includes the information of the divided region R in which the intersection point IP is present and the positional information of the intersection point IP.

Figure 16:
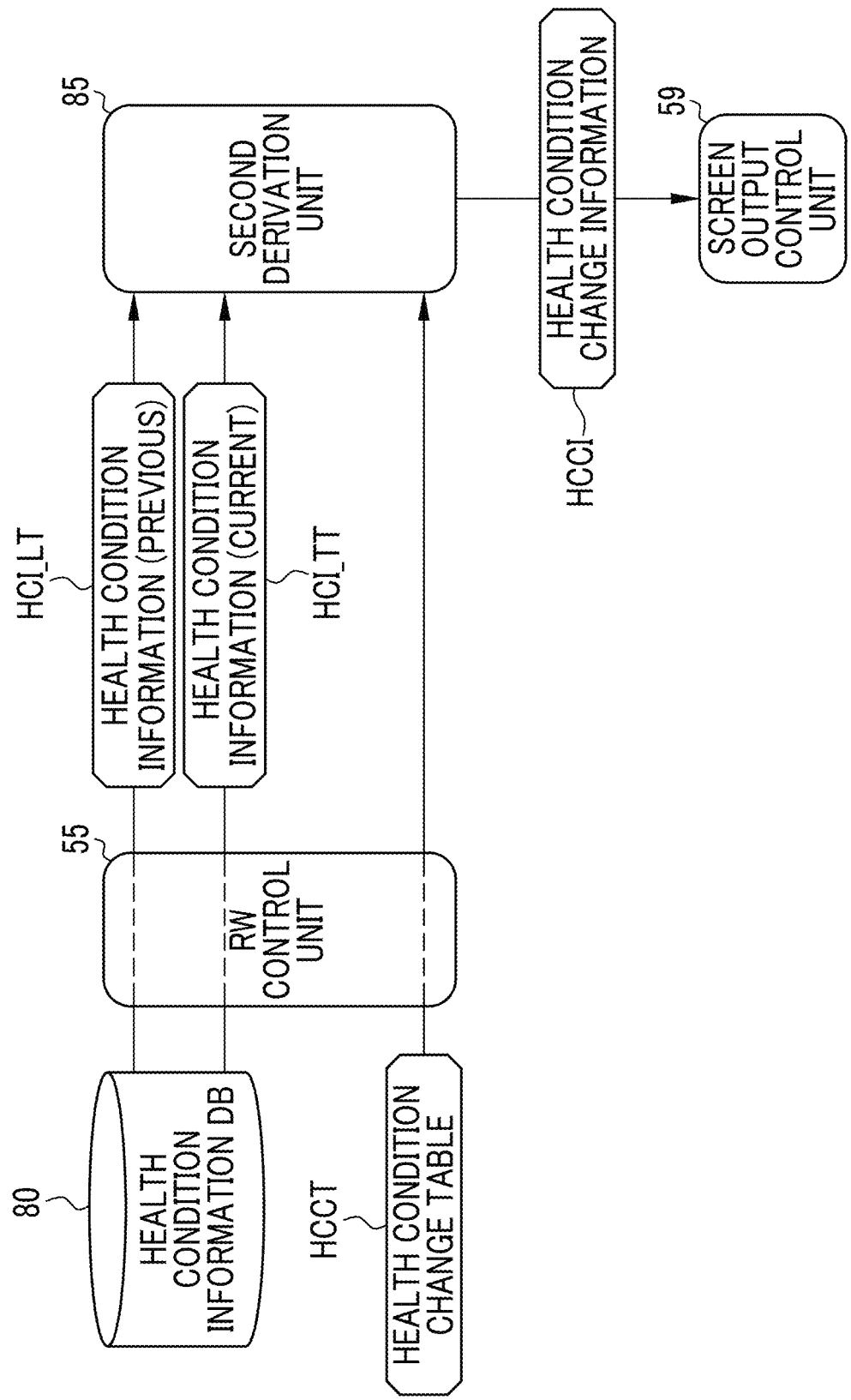
FIG. 16 is a diagram illustrating a second embodiment comprising a second derivation unit that derives a change in the health conditions of a pet.

In FIG. 16, a CPU 42A of the health management apparatus according to the second embodiment functions as a second derivation unit 85 in addition to each unit of the first embodiment (only the RW control unit 55 and the screen output control unit 59 are illustrated in FIG. 16). Further, in addition to the health condition information DB 80, a health condition change table HCCT is stored in the storage device 40A of the health management apparatus according to the second embodiment.

The RW control unit 55 reads previous health condition information HCI_LT and current health condition information HCI_TT of the target pet TP from the health condition information DB 80. The RW control unit 55 outputs the read previous health condition information HCI_LT and current health condition information HCI_TT of the target pet TP to the second derivation unit 85. In addition, the RW control unit 55 reads the health condition change table HCCT from the storage device and outputs the read health condition change table HCCT to the second derivation unit 85.

The second derivation unit 85 derives a change in the health condition of the target pet TP on the basis of the previous health condition information HCI_LT and the current health condition information HCI_TT of the target pet TP and the health condition change table HCCT from the RW control unit 55. The second derivation unit 85 creates health condition change information HCCI indicating the derived change in the health condition and outputs the health condition change information HCCI to the screen output control unit 59. The screen output control unit 59 performs control to output the change in the health condition on the basis of the health condition change information HCCI (see FIG. 20). The previous health condition information HCI_LT of the target pet TP is an example of a "correlation between a previous obesity parameter and a previous bone parameter of a target subject" according to the technology of the present disclosure. In addition, the current health condition information HCI_TT of the target pet TP is an example of a "correlation between a current obesity parameter and a current bone parameter of a target subject" according to the technology of the present disclosure.

As illustrated in FIG. 17, the health condition change table HCCT is a table in which a change in the health condition corresponding to a previous region and a current region has been registered. The previous region is a divided region R in which an intersection point IP_LT (see FIG. 20) of the obesity parameter and the bone parameter in the previous medical examination is present. The current region is a divided region R in which an intersection point IP_TT (see FIG. 20) of the obesity parameter and the bone parameter in the current medical examination is present.

In the health condition change table HCCT, for example, "obesity progresses due to overeating" is registered as the change in the health condition in the previous regions R_A1 and R_A2 and the current region R_B. Further, for example, "there is a possibility of hormone imbalance" is registered as the change in the health condition in the previous region R_B and the current region R_F. In addition, for example, "obesity has been improved" is registered as the change in the health condition in the previous region R_B and the current region R_A2.

Figure 18:
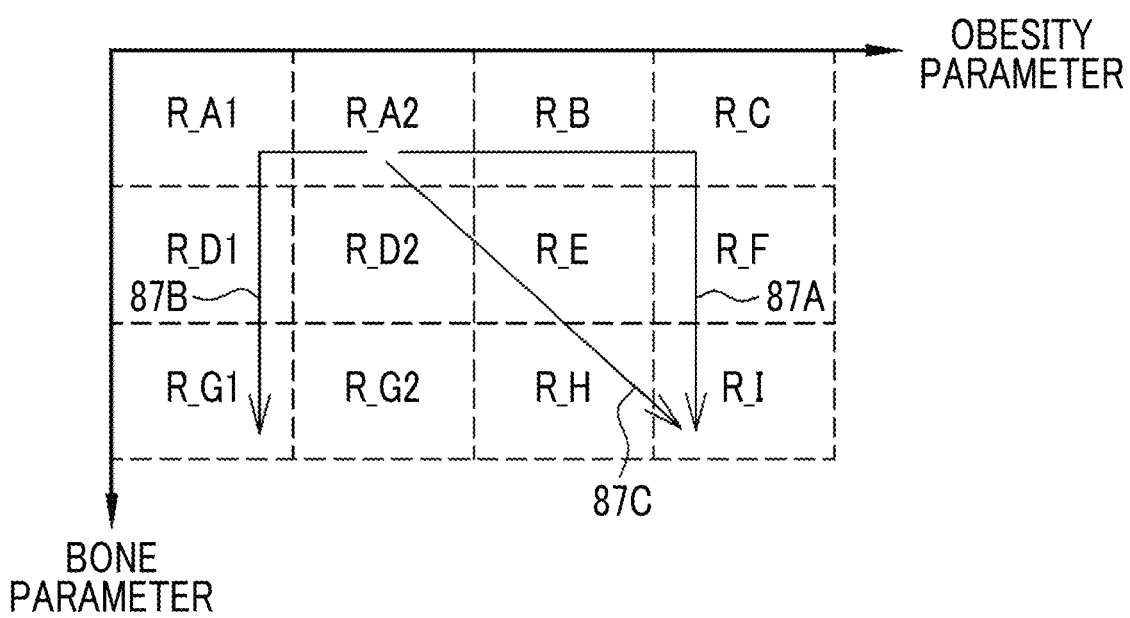
FIG. 18 is a diagram illustrating determination which is the creation source of the health condition change table.

As illustrated in FIG. 18, in the health condition table HCCT, a change in the divided region R along an arrow 87A in the coordinate region CR is created on the basis of the determination that obesity or diabetes has progressed due to overeating or that diabetes may develop due to overeating. In addition, in the health condition change table HCCT, a change in the divided region R along an arrow 87B in the coordinate region CR is created on the basis of the determination that osteoporosis may develop with aging or that osteoporosis has progressed with aging. Further, in the health condition change table HCCT, a change in the divided region R along the arrow 87C in the coordinate region CR is created on the basis of the determination that a hormone imbalance has occurred or that obesity and osteoporosis have progressed due to a hormone imbalance.

Figure 19:
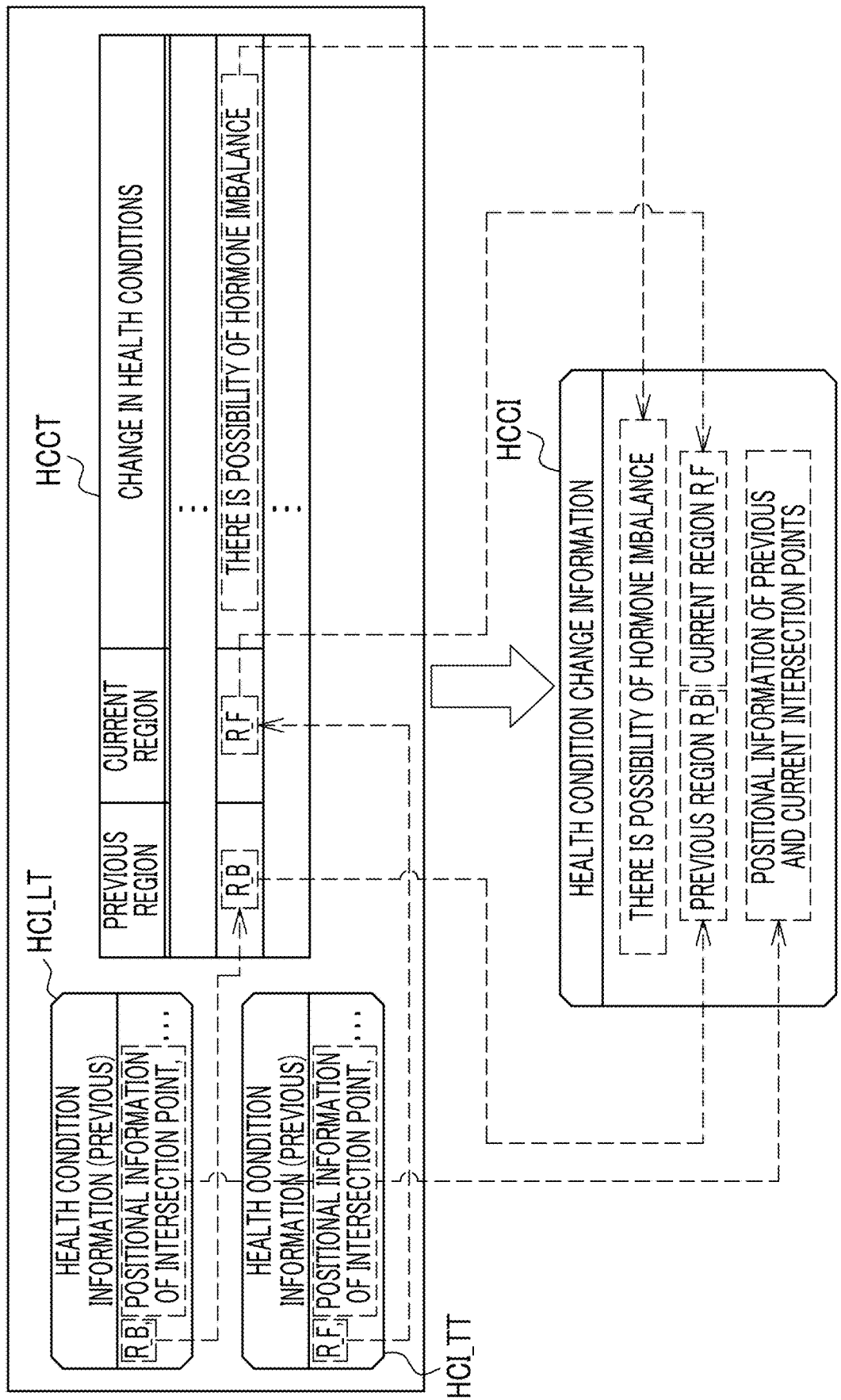
FIG. 19 is a diagram illustrating an aspect in which the second derivation unit derives a change in the health conditions of the target pet.

As illustrated in FIG. 19, the second derivation unit 85 derives a change in the health condition corresponding to the previous region of the target pet TP included in the previous health condition information HCI_LT and the current region of the target pet TP included in the current health condition information HCI_TT from the health condition change table HCCT. The second derivation unit 85 creates the health condition change information HCCI including the derived change in the health condition, the previous region and the current region corresponding to the change in the health condition, the positional information of the previous intersection point IP_LT, and the positional information of the current intersection point IP_TT. FIG. 19 illustrates an example in which the previous region of the target pet TP included in the previous health condition information HCI_LT is R_B, the current region of the target pet TP included in the current health condition information HCI_TT is R_F, and "there is a possibility of hormone imbalance" which is a change in the health condition corresponding to the previous and current regions has been derived.

Figure 20:
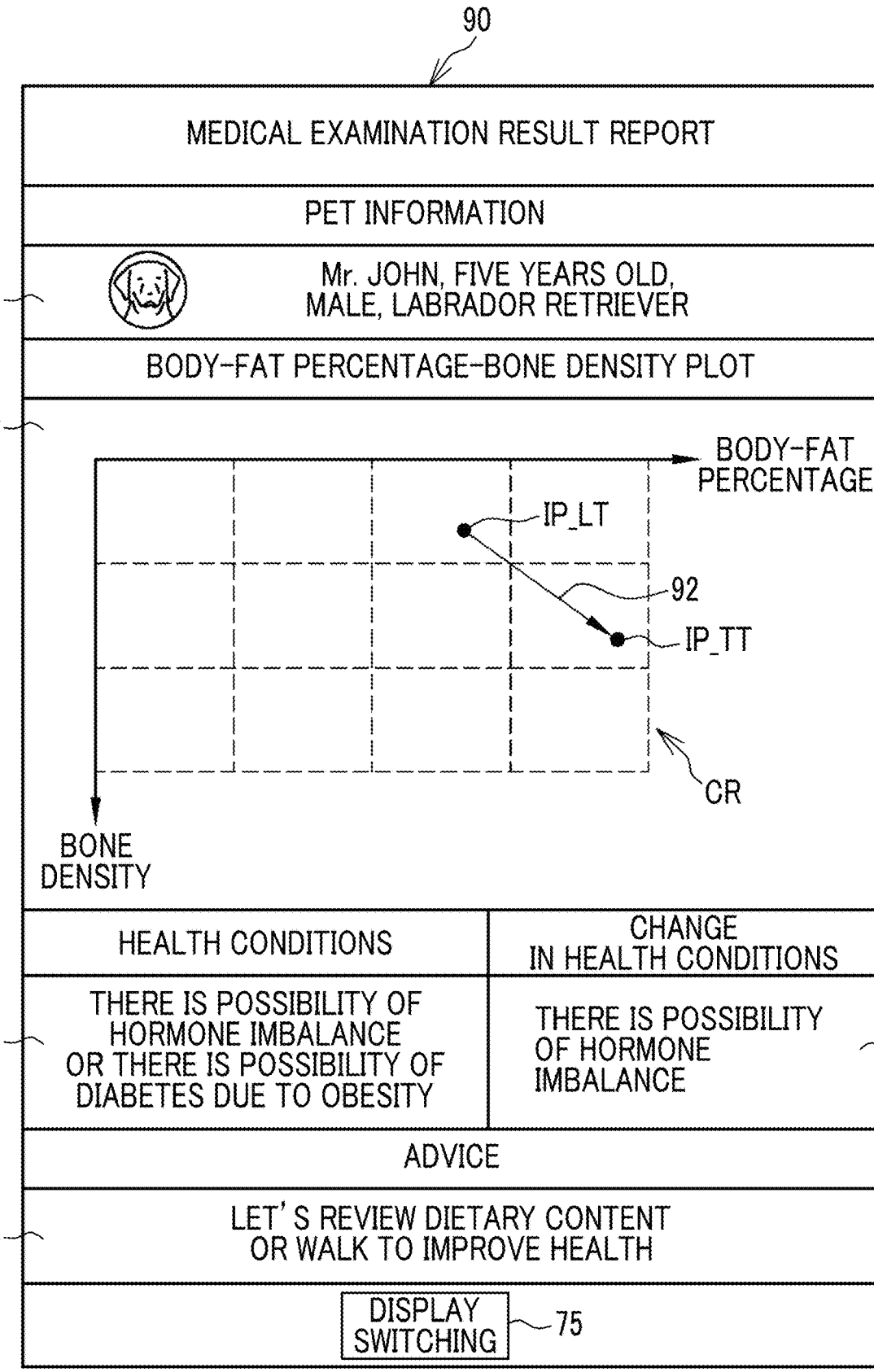
FIG. 20 is a diagram illustrating a medical examination result display screen according to the second embodiment.

In FIG. 20, in addition to the sections 71 to 74 of the medical examination result display screen 70 according to the first embodiment, a health condition change display section 91 is provided on a medical examination result display screen 90 according to the second embodiment. The change in the health condition of the target pet TP derived by the second derivation unit 85 is displayed in the health condition change display section 91. In addition, a previous intersection point IP_LT, a current intersection point IP_TT, and an arrow 92 that has the intersection point IP_LT as a starting point and has the intersection point IP_TT as an end point are displayed in the coordinate region display section 72 of the medical examination result display screen 90.

As such, in the second embodiment, the second derivation unit 85 derives a change in the health condition of the target pet TP on the basis of the correlation between the previous obesity parameter and bone parameter of the target pet TP and the correlation between the current obesity parameter and bone parameter of the target pet TP. The screen output control unit 59 performs control to output the change in the health condition through the medical examination result display screen 90. Therefore, it is possible to simply recognize whether the health condition of the target pet TP has deteriorated or improved from the previous medical examination.

The second derivation unit 85 derives a change in the health condition of the target pet TP using the health condition change table HCCT. Specifically, the health condition change table HCCT is a table in which a change in the health condition corresponding to the previous region that is a divided region R in which the intersection point IP_LT of the previous obesity parameter and bone parameter of the target pet TP is present and the current region that is a divided region R in which the intersection point IP_TT of the current obesity parameter and bone parameter of the target pet TP is present has been registered. Then, the second derivation unit 85 derives a change in the health condition corresponding to the previous region and the current region of the target pet TP from the health condition change table HCCT. Therefore, it is possible to very simply derive a change in the health condition of the target pet TP.

The screen output control unit 59 performs control to output the coordinate region CR including the intersection point IP_LT of the previous obesity parameter and bone parameter of the target pet TP and the intersection point IP_TT of the current obesity parameter and bone parameter of the target pet TP through the medical examination result display screen 90. Therefore, it is possible to more simply recognize whether the health condition of the target pet TP has deteriorated or improved from the previous medical examination.

In a case in which the previous region and the current region of the target pet TP are the same, it may be assumed that there is no change in the health condition and the display of the health condition change display section 91 and the intersection point IP_LT of the previous obesity parameter and bone parameter may be stopped.

A change in the health condition of the target pet TP may be derived not from a change in the divided region R but from the direction and inclination of a vector connecting the intersection point IP_LT of the previous obesity parameter and bone parameter of the target pet TP and the intersection point IP_TT of the current obesity parameter and bone parameter of the target pet TP.

Third Embodiment

In a third embodiment illustrated in FIGS. 21 to 24, a similar pet SP having a similar change in the health condition to the target pet TP is searched and the change in the health condition of the similar pet SP is output. The similar pet SP is an example of a "similar subject" according to the technology of the present disclosure.

Figure 21:
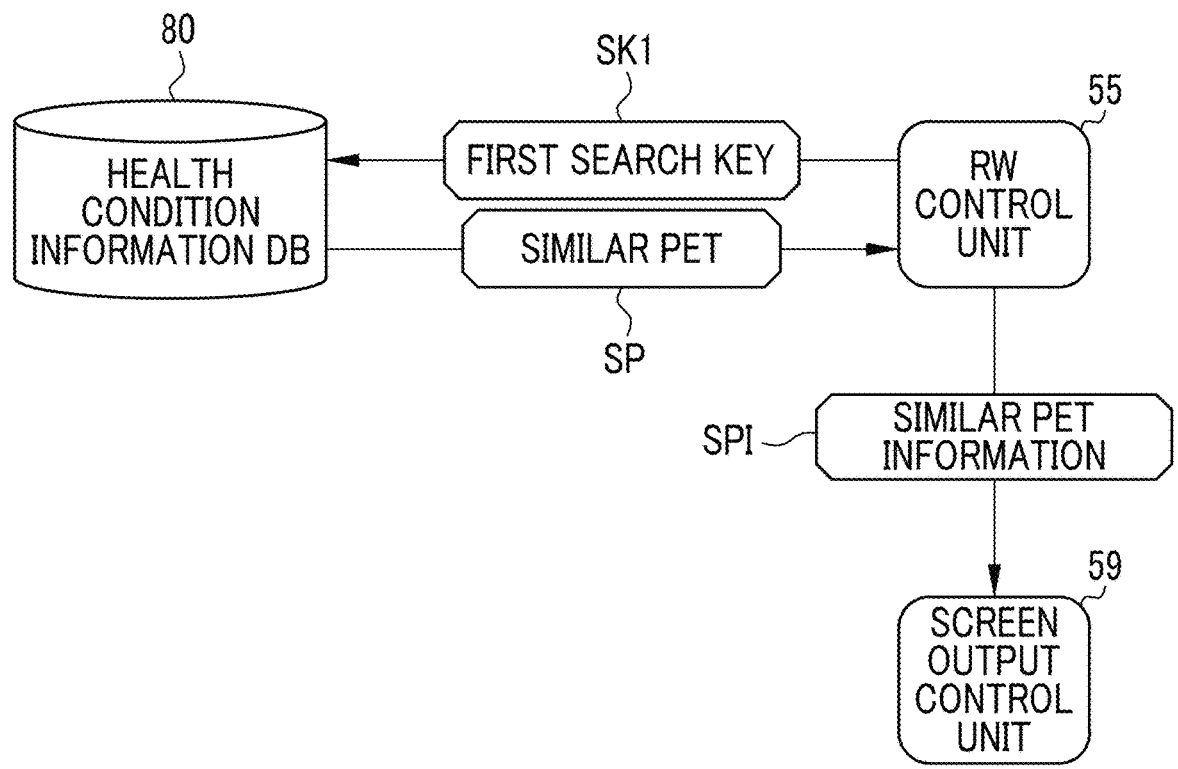
FIG. 21 is a diagram illustrating a third embodiment in which a similar pet is searched.

In FIG. 21, an RW control unit 55 according to the third embodiment outputs a first search key SK1 for searching for the similar pet SP to the health condition information DB 80. The health condition information DB 80 outputs the similar pet SP corresponding to the first search key SK1 to the RW control unit 55. That is, the RW control unit 55 is an example of a "first search unit" according to the technology of the present disclosure. The RW control unit 55 creates similar pet information SPI which is information of the similar pet SP and outputs the similar pet information SPI to the screen output control unit 59.

Figure 22:
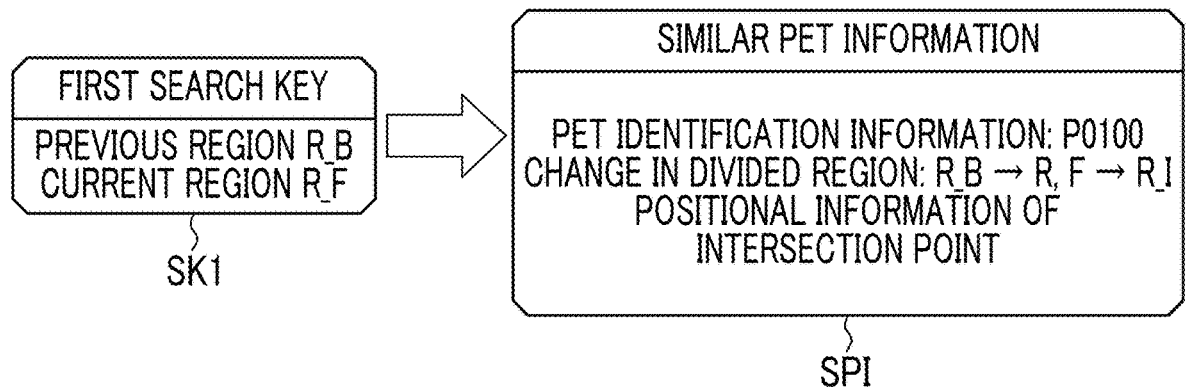
FIG. 22 is a diagram illustrating an example of a first search key and similar pet information.

As illustrated in FIG. 22, the first search key SK1 includes the previous region and the current region of the target pet TP. The RW control unit 55 acquires a pet having a change in the divided region R that is the same as a change in the previous region and the current region of the target pet TP in the first search key SK1 as the similar pet SP from the health condition information DB 80. The RW control unit 55 creates the similar pet information SPI including the pet identification information of the similar pet SP, a change in the divided region R, and the positional information of the intersection point. FIG. 22 illustrates a case in which the previous region of the target pet TP is R_B and the current region thereof is R_F. A case in which a pet that has pet identification information "P0100" and has a change in the divided region R in the order of R_B→R_F→R_I which is the same as a change in the previous region and the current region of the target pet TP is searched as the similar pet SP will be described as an example.

The first search key SK1 also includes the pet information of the target pet TP, such as an animal species, a breed, sex, and age. The RW control unit 55 searches for a similar pet SP having the same animal species, breed, sex, and age as the target pet TP. The first search key SK1 may include the length, height, and abdominal circumference of the target pet TP or the disease of the target pet TP and the similar pet SP whose length, height, abdominal circumference, or disease is as similar to that of the target pet TP as possible may be searched.

Figure 23:
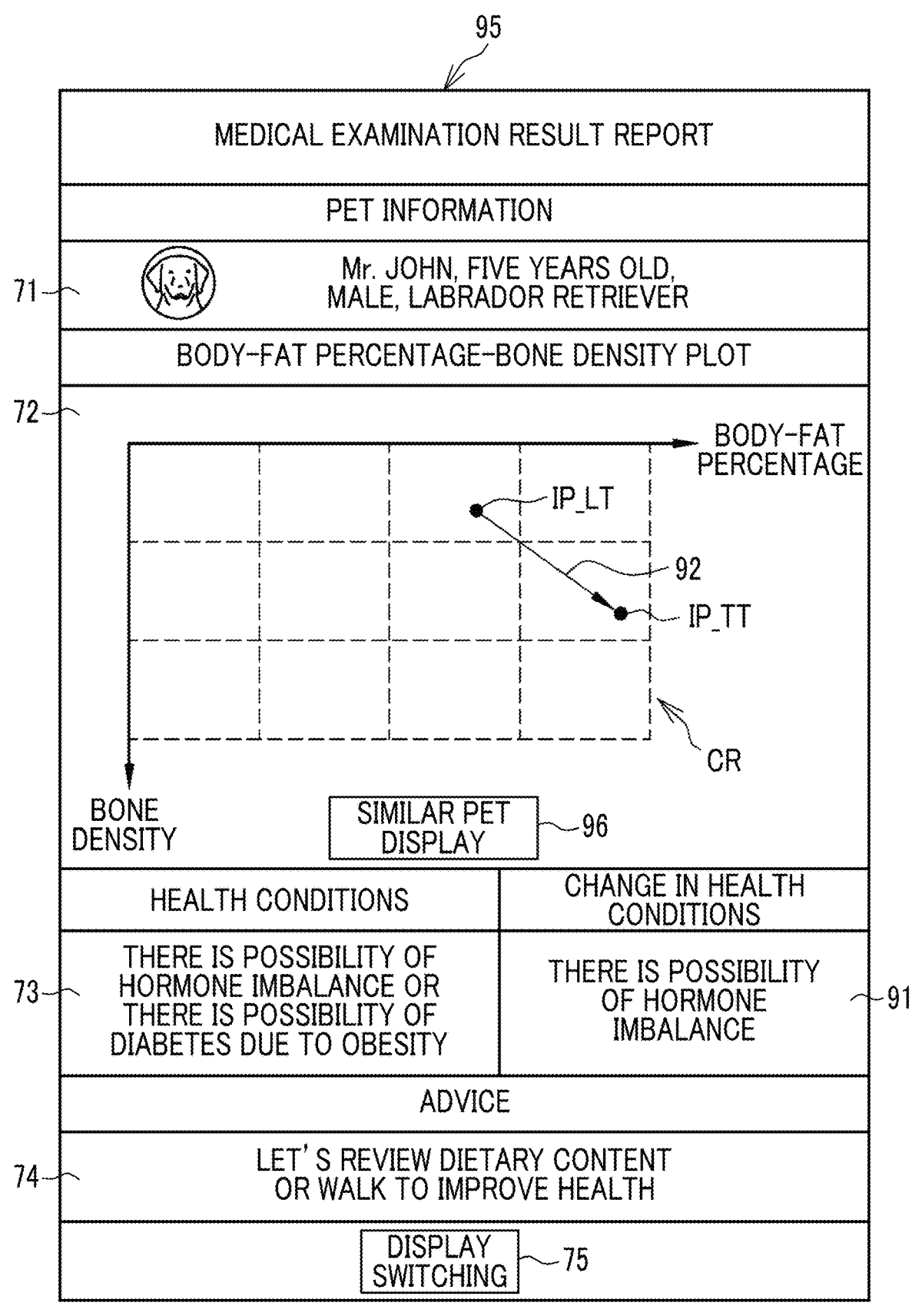

In FIGS. 23 and 24, a similar pet display button 96 is provided in a coordinate region display section 72 of a medical examination result display screen 95 according to the third embodiment. The medical examination result display screen 95 illustrated in FIG. 23 is displayed before the similar pet display button 96 is pressed and the medical examination result display screen 95 illustrated in FIG. 24 is displayed after the similar pet display button 96 is pressed.

In a case the similar pet display button 96 is pressed, the RW control unit 55 searches for the similar pet SP. As a result, as illustrated in FIG. 24, in addition to the intersection point IP_LT of the previous obesity parameter and bone parameter of the target pet TP, the intersection point IP_TT of the current obesity parameter and bone parameter of the target pet TP, and the arrow 92, a change HCC_SP in the health condition of the similar pet SP is displayed on the medical examination result display screen 95. Specifically, the change HCC_SP in the health condition of the similar pet SP includes an intersection point IP_SP of the obesity parameter and the bone parameter of the similar pet SP and an arrow 97 connecting the intersection point IP_SP.

As such, in the third embodiment, the RW control unit 55 searches for the similar pet SP having a similar change in the health condition to the target pet TP. The screen output control unit 59 performs control to output the change HCC_SP in the health condition of the similar pet SP through the medical examination result display screen 95. Therefore, it is possible to predict a change in the health condition of the target pet TP from the change HCC_SP in the health condition of the similar pet SP. In a case in which a change in the health condition of the similar pet SP indicates deterioration, it is possible to notify the risk of the health condition deteriorating as it stands and to motivate the owner to take positive action for improvement.

In addition, the screen output control unit 59 performs control to output the coordinate region CR including the intersection point IP_SP of the obesity parameter and the bone parameter of the similar pet SP, in addition to the intersection point IP_LT of the previous obesity parameter and bone parameter of the target pet TP and the intersection point IP_TT of the current obesity parameter and bone parameter of the target pet TP, through the medical examination result display screen 95. Therefore, it is possible to easily compare a change in the health condition of the target pet TP with the change HCC_SP in the health condition of the similar pet SP.

Fourth Embodiment

In a fourth embodiment illustrated in FIGS. 25 to 30, in a case in which the content of a change in the health condition of the target pet TP indicates deterioration, prescription information PI on an improved pet BP whose health condition is inversely changing to improvement is searched and the searched prescription information PI is output. The improved pet BP is an example of an "improved subject" according to the technology of the present disclosure.

Figure 25:
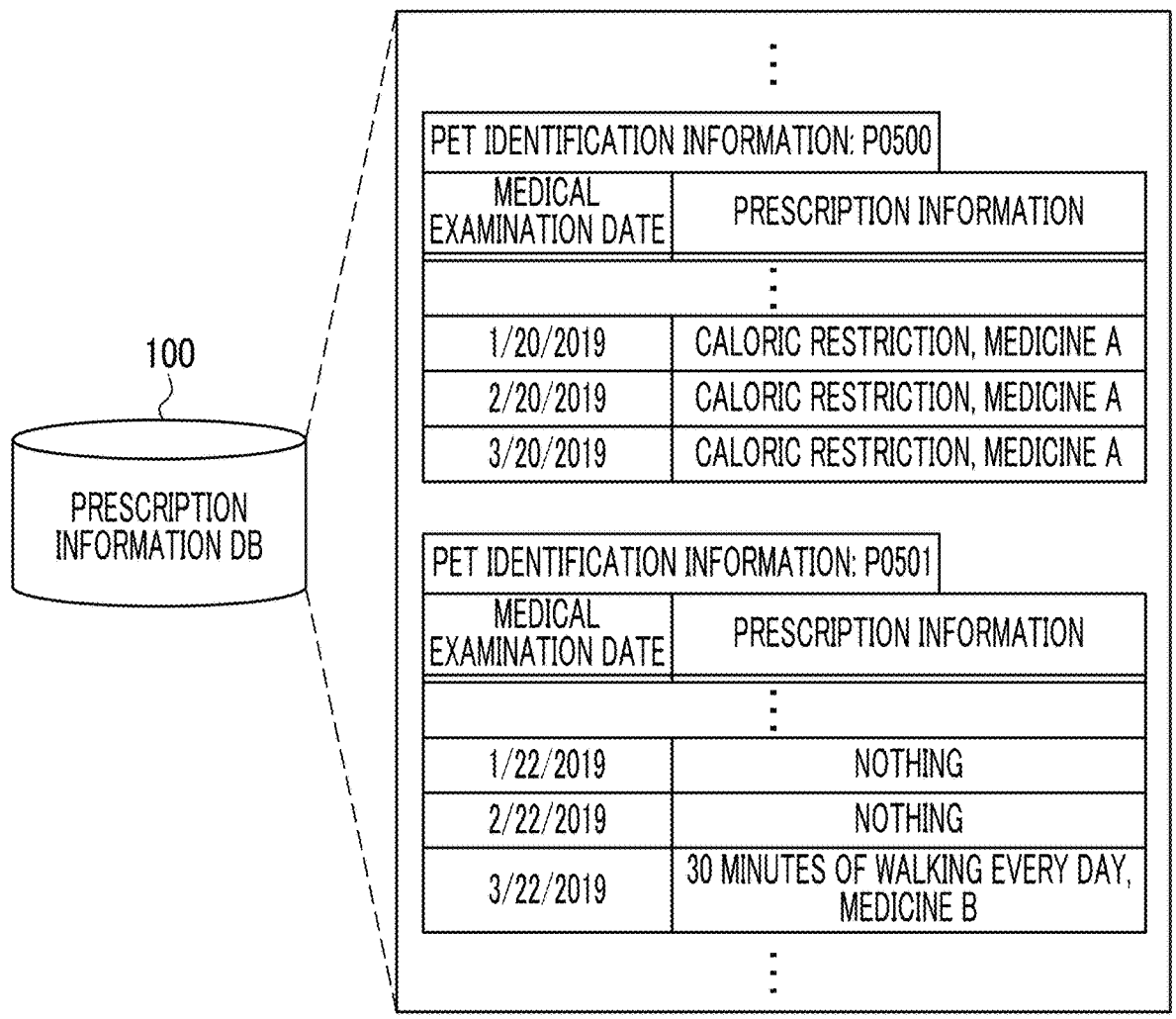
FIG. 25 is a diagram illustrating a prescription information DB.

In FIG. 25, a prescription information DB 100 is stored in a storage device 40A of a health management apparatus according to the fourth embodiment. In the prescription information DB 100, a set of a medical examination date and the prescription information PI is registered for each pet identification information item. The prescription information PI is information related to dietary restrictions and exercise recommended for each pet and medicines administered to each pet, such as "a caloric restriction and a medicine A" and "30 minutes of walking every day and a medicine B".

Figure 26:
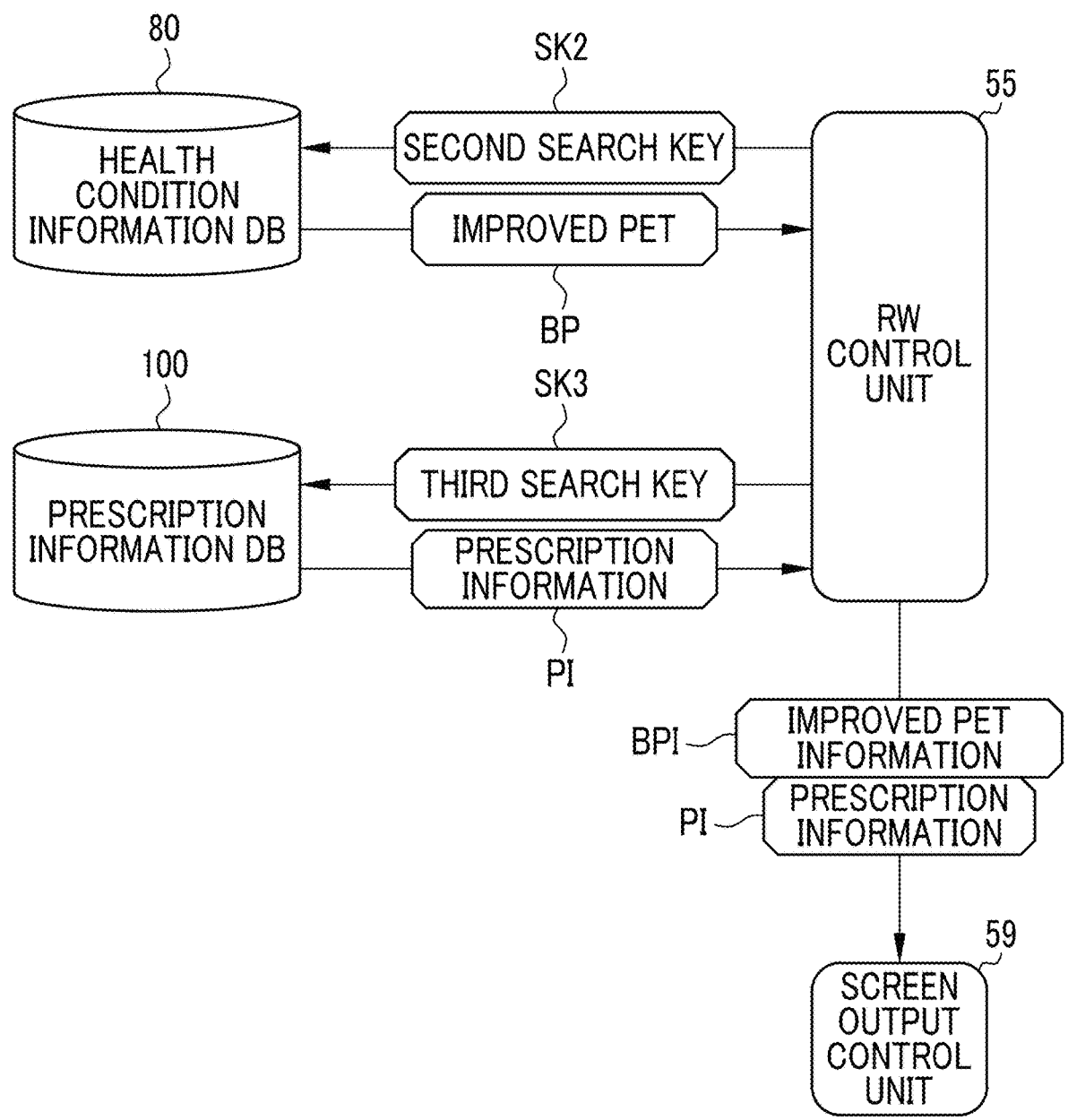
FIG. 26 is a diagram illustrating a fourth embodiment in which prescription information on an improved subject is searched.

In FIG. 26, the RW control unit 55 according to the fourth embodiment outputs a second search key SK2 for searching for the improved pet BP to the health condition information DB 80. The health condition information DB 80 outputs the improved pet BP corresponding to the second search key SK2 to the RW control unit 55. The RW control unit 55 creates improved pet information BPI which is information of the improved pet BP and outputs the improved pet information BPI to the screen output control unit 59.

In addition, the RW control unit 55 outputs a third search key SK3 for searching for the prescription information PI of the improved pet BP to the prescription information DB 100. The prescription information DB 100 outputs prescription information PI corresponding to the third search key SK3 to the RW control unit 55. That is, the RW control unit 55 is an example of a "second search unit" according to the technology of the present disclosure. The RW control unit 55 outputs the prescription information PI of the improved pet BP to the screen output control unit 59.

Figure 27:
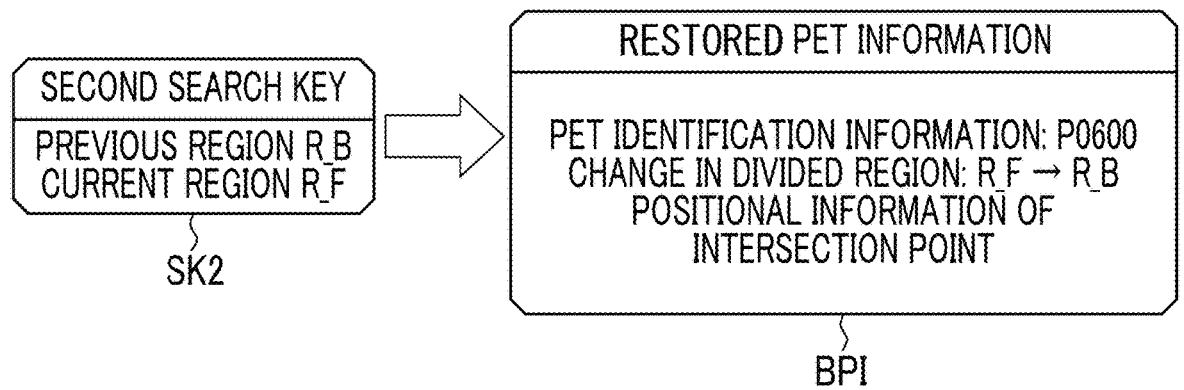
FIG. 27 is a diagram illustrating an example of a second search key and restored pet information.

As illustrated in FIG. 27, the second search key SK2 includes the previous region and the current region of the target pet TP, similarly to the first search key SK1 according to the third embodiment. The RW control unit 55 acquires a pet in which a change in the divided region R is reverse to a change in the previous region and the current region of the target pet TP in the second search key SK2 as the improved pet BP from the health condition information DB 80. The RW control unit 55 creates the improved pet information BPI including the pet identification information of the improved pet BP, a change in the divided region R, and the positional information of the intersection point. FIG. 27 illustrates a case in which the previous region of the target pet TP is R_B and the current region thereof is R_F. In addition, FIG. 27 illustrates a case in which a pet that has pet identification information "P0600" and has a change in the divided region R from R_F to R_B which is reverse to a change in the previous region and the current region of the target pet TP is searched as the improved pet BP.

Similarly to the first search key SK1, the second search key SK2 also includes the pet information of the target pet TP, such as an animal species, a breed, sex, and age. The RW control unit 55 searches for an improved pet BP having the same animal species, breed, sex, and age as the target pet TP. Similarly to the first search key SK1, the second search key SK2 may include the length, height, and abdominal circumference of the target pet TP or the disease of the target pet TP and the improved pet BP whose length, height, abdominal circumference, or disease is as similar to that of the target pet TP as possible may be searched.

Figure 28:
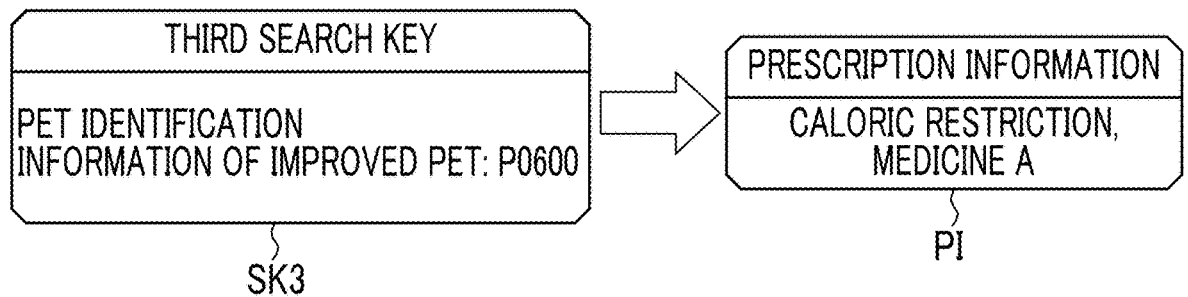
FIG. 28 is a diagram illustrating an example of a third search key and prescription information.

As illustrated in FIG. 28, the third search key SK3 includes the pet identification information of the improved pet BP. The RW control unit 55 acquires the latest prescription information PI corresponding to the pet identification information of the improved pet BP in the third search key SK3 from the prescription information DB 100. FIG. 28 illustrates a case in which the pet identification information of the improved pet BP is "P0600" and the prescription information PI is "a caloric restriction and a medicine A".

Figure 29:
FIG. 29 is a diagram illustrating a medical examination result display screen according to the fourth embodiment in which prescription information on an improved pet is not displayed.

In FIGS. 29 and 30, an improved pet display button 106 is provided in a coordinate region display section 72 of a medical examination result display screen 105 according to the fourth embodiment. The medical examination result display screen 105 illustrated in FIG. 29 is displayed before the improved pet display button 106 is pressed and the medical examination result display screen 105 illustrated in FIG. 30 is displayed after the improved pet display button 106 is pressed.

In a case in which the improved pet display button 106 is pressed, the RW control unit 55 searches for the prescription information PI of the improved pet BP. As a result, as illustrated in FIG. 30, a change HCC_BP in the health condition of the improved pet BP is displayed on the medical examination result display screen 105 in addition to the intersection point IP_LT of the previous obesity parameter and bone parameter of the target pet TP, the intersection point IP_TT of the current obesity parameter and bone parameter of the target pet TP, and the arrow 92. Specifically, the change HCC_BP in the health condition of the improved pet BP includes an intersection point IP_BP of the obesity parameter and the bone parameter of the improved pet BP and an arrow 107 connecting the intersection point IP_BP. In addition, a balloon 108 indicating the prescription information PI of the improved pet BP is displayed in the coordinate region display section 72.

As such, in the fourth embodiment, in a case in which the content of a change in the health condition of the target pet TP indicates deterioration, the RW control unit 55 searches for the prescription information PI on the improved pet BP whose health condition is inversely changing to improvement. The screen output control unit 59 performs control to output the prescription information PI on the improved pet BP through the medical examination result display screen 105. Therefore, the prescription information PI of the improved pet BP can be used as a model for improving the health condition of the target pet TP.

Figure 31:
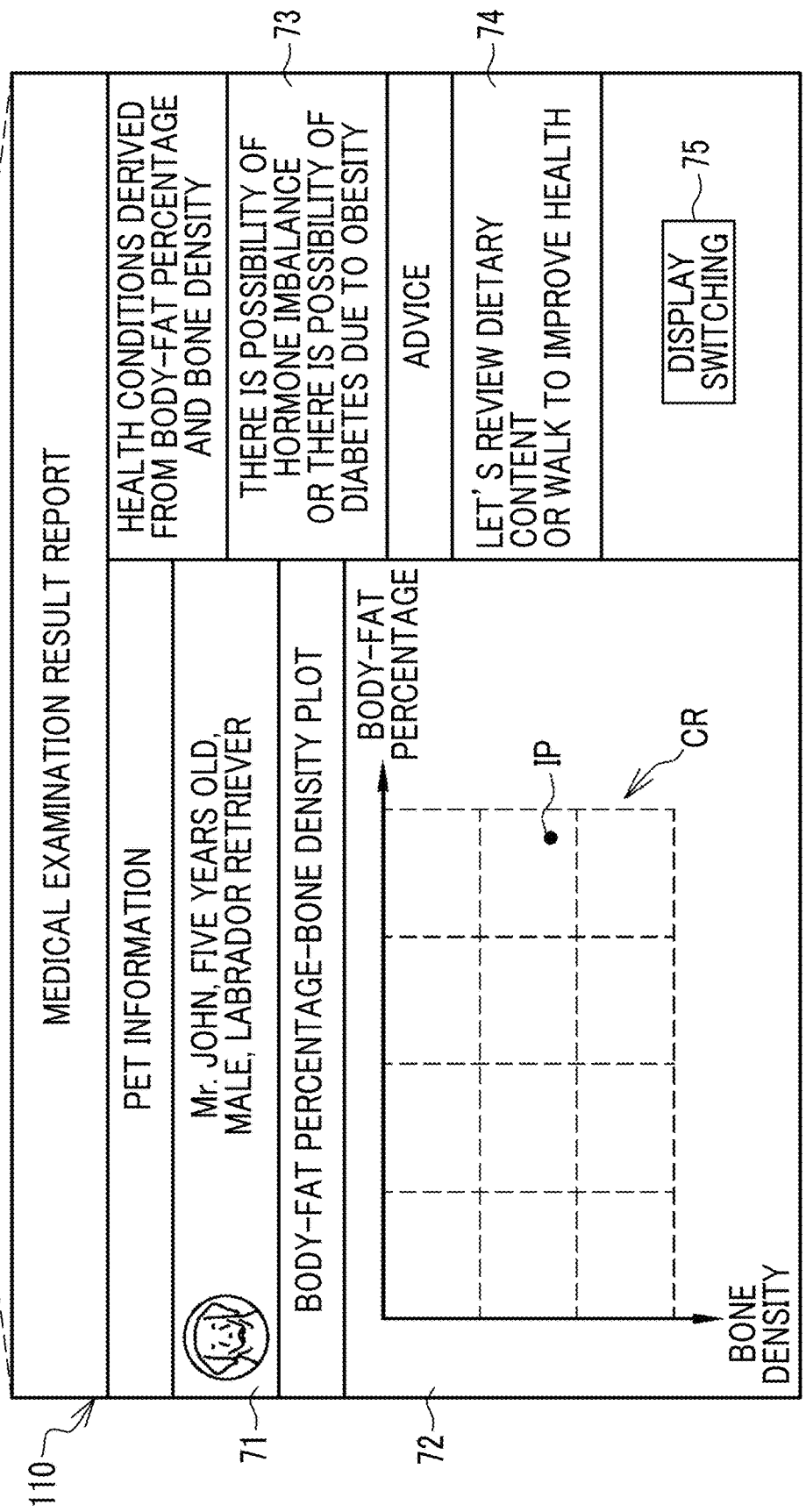
FIG. 31 is a diagram illustrating a medical examination result display screen in a case in which a display of the owner terminal is aligned in the horizontal direction.

In each of the above-described embodiments, as illustrated in, for example, FIG. 11, it is assumed that the display 44B of the owner terminal 11 is aligned in the vertical direction and the medical examination result display screen in which the sections 71 to 74 are arranged in the vertical direction is displayed as an example. However, the present disclosure is not limited thereto. As in a medical examination result display screen 110 illustrated in FIG. 31, a case in which the display 44B of the owner terminal 11 is aligned in the horizontal direction may be assumed, the pet information display section 71 and the coordinate region display section 72 may be laid out on the left side, and the health condition display section 73 and the advice display section 74 may be laid out on the right side. It is preferable that the display of the vertical medical examination result display screen illustrated in, for example, FIG. 11 and the horizontal medical examination result display screen 110 illustrated in FIG. 31 is switched according to the direction of the display 44B of the owner terminal 11.

The method of dividing the coordinate region CR is not limited to the division of the coordinate region CR into twelve equal regions described in each of the above-described embodiments.

It is preferable that the health condition table HCT and the health condition change table HCCT are provided for each animal species of the target pet TP. In addition, the health condition table HCT and the health condition change table HCCT may be provided for each breed of the target pet TP. Examples of the animal species of the target pet TP include dogs, cats, birds, rabbits, and hamsters. In a case in which the animal species of the target pet TP is a dog, examples of the breed of the target pet TP include Labrador Retriever, Shiba Inu, Chihuahua, Weimaraner, Yorkshire Terrier, Papillon, and Maltese. In a case in which the animal species of the target pet TP is a cat, examples of the breed of the target pet TP include Ragdoll, Himalayan, and Ragamuffin.

The health condition table HCT and the health condition change table HCCT may be subdivided by sex and age. In addition, the health condition table HCT and the health condition change table HCCT may be divided according to whether or not castration surgery has been performed.

In each of the above-described embodiments, the medical examination result display screen 70 is given as an example of the output form of the coordinate region CR including the health condition of the target pet TP and the intersection point IP of the obesity parameter and the bone parameter of the target pet TP. However, the invention is not limited thereto. Instead of or in addition to, for example, the medical examination result display screen 70, an aspect in which the coordinate region CR is printed out on a paper medium or an aspect in which the coordinate region CR is output as a data file may be adopted. For the coordinate region CR including a change in the health condition of the target pet TP, the intersection point IP_LT of the previous obesity parameter and bone parameter of the target pet TP, and the intersection point IP_TT of the current obesity parameter and bone parameter of the target pet TP, similarly, instead of or in addition to, for example, the medical examination result display screen 90, an aspect in which the coordinate region CR is printed out on a paper medium or an aspect in which the coordinate region CR is output as a data file may be adopted.

For the coordinate region CR including the change HCC_SP in the health condition of the similar pet SP and the intersection point IP_SP of the obesity parameter and the bone parameter of the similar pet SP, similarly, instead of or in addition to the medical examination result display screen 95, an aspect in which the coordinate region CR is printed out on a paper medium or an aspect in which the coordinate region CR is output as a data file may be adopted. Further, for the prescription information PI on the improved pet BP, similarly, instead of or in addition to the medical examination result display screen 105, an aspect in which the prescription information PI is printed out on a paper medium or an aspect in which the prescription information PI is output as a data file may be adopted.

A human may be the target subject.

The owner terminal 11 and/or the hospital terminal 12 may function as the health management apparatus 10.

The hardware configuration of the computer forming the health management apparatus 10 can be modified in various ways. For example, the health management apparatus 10 may be configured by a plurality of computers which are separated as hardware in order to improve processing capability and reliability. Specifically, the functions of the RW control unit 55 and the calculation unit 56 and the functions of the acquisition unit 57, the first derivation unit 58, and the screen output control unit 59 are distributed to two server computers. In this case, the two server computers form the health management apparatus 10.

As described above, the hardware configuration of the computer can be appropriately changed depending on the required performance such as processing capability, safety, and reliability. In addition to hardware, an AP, such as the operation program 50, may be duplicated or may be dispersively stored in a plurality of storage devices in order to ensure safety and reliability.

In the above-described embodiments, for example, the following various processors can be used as the hardware structure of processing units performing various processes, such as the RW control unit 55, the calculation unit 56, the acquisition unit 57, the first derivation unit 58, the screen output control unit 59 (the screen generation unit 60 and the screen transmission unit 61), and the second derivation unit 85. The various processors include the CPU 42A which is a general-purpose processor executing software to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to recognize the invention described in the following Supplementary Note 1 from the above description.

Supplementary Note 1

There is provided a health management apparatus comprising: an acquisition processor that acquires an obesity parameter indicating a degree of obesity of a target subject and a bone parameter indicating a degree of bone strength of the target subject; a first derivation processor that derives a health condition of the target subject on the basis of a correlation between the obesity parameter and the bone parameter; and an output control processor that performs control to output the health condition.

In the technology according to the present disclosure, the above-described various embodiments and/or various modifications may be appropriately combined with each other. For example, the first embodiment and the second embodiment may be combined with each other to derive and output the health condition of the target pet TP and a change in the health condition of the target pet TP. Alternatively, the third embodiment and the fourth embodiment may be combined with each other to search for the prescription information PI for the similar pet SP and the improved pet BP and to output the change HCC_SP in the health condition of the similar pet SP and the prescription information PI on the improved pet BP.

The technology according to the present disclosure is not limited to each of the above-described embodiments and can adopt various configurations without departing from the scope and spirit of the present disclosure. In addition, the technology according to the present disclosure may be applied to a program and a storage medium that non-transitorily stores the program.

The contents described and illustrated above are the detailed description of portions related to the technology according to the present disclosure and are merely examples of the technology according to the present disclosure. For example, the description of the configurations, the functions, the operations, and the effects is the description of an example of the configurations, functions, operations, and effects of a portion according to the technology of the present disclosure. Therefore, for the contents described and illustrated above, unnecessary portions may be deleted or new elements may be added or replaced without departing from the scope and spirit of the technology according to the present disclosure. In the contents described and illustrated above, the description of common technical knowledge that does not require any explanation in order to enable the implementation of the technology according to the present disclosure is omitted in order to avoid complications and facilitate the understanding of the portions related to the technology according to the present disclosure.

In the specification, "A and/or B" is synonymous with "at least one of A or B". That is, "A and/or B" means A, B, or a combination of A and B. In the specification, the same concept as "A and/or B" is applied to a case in which three or more things are expressed by connecting them with "and/or".

All of the documents, the patent applications, and the technical standards described in the specification are incorporated by reference to the same extent as the incorporation of each of the documents, the patent applications and the technical standards by reference is specifically and individually stated.

What is claimed is:

1. A health management apparatus comprising:
    an acquisition unit that acquires an obesity parameter indicating a degree of obesity of a target subject and a bone parameter indicating a degree of bone strength of the target subject;
    a first derivation unit that derives a health condition of the target subject on the basis of a correlation between the obesity parameter and the bone parameter;
    an output control unit that performs control to output the health condition; and
    a reading unit that reads, from a storage unit, a health condition table in which health conditions have been registered, each of the health conditions corresponding to one of a plurality of divided regions obtained by dividing a coordinate region in which the obesity parameter is disposed on one of a vertical axis and a horizontal axis and the bone parameter is disposed on the other axis, and that outputs the health condition table to the first derivation unit,
    wherein the health condition of the target subject is derived by the first derivation unit from the health condition table and corresponds to a divided region in which an intersection point of the obesity parameter and the bone parameter of the target subject is present.

2. The health management apparatus according to claim 1, wherein the output control unit performs control to output the coordinate region including the intersection point of the obesity parameter and the bone parameter of the target subject.

3. The health management apparatus according to claim 1, further comprising:
    a second derivation unit that derives a change in the health condition of the target subject on the basis of a correlation between a previous obesity parameter and a previous bone parameter of the target subject and a correlation between a current obesity parameter and a current bone parameter of the target subject,
    wherein the output control unit performs control to output the change in the health condition.

4. The health management apparatus according to claim 3, wherein the reading unit reads, from the storage unit, a health condition change table in which a change in the health condition corresponding to a previous region that is the divided region including the intersection point of the previous obesity parameter and the previous bone parameter and a current region that is the divided region including the intersection point of the current obesity parameter and the current bone parameter has been registered and outputs the health condition change table to the second derivation unit, and
    the second derivation unit derives the change in the health condition corresponding to the previous region and the current region of the target subject from the health condition change table.

5. The health management apparatus according to claim 4, wherein the output control unit performs control to output the coordinate region including the intersection point of the previous obesity parameter and the previous bone parameter of the target subject and the intersection point of the current obesity parameter and the current bone parameter of the target subject.

6. The health management apparatus according to claim 5, further comprising:
    a first search unit that searches for a similar subject having a similar change in the health condition to the target subject,
    wherein the output control unit performs control to output a change in the health condition of the similar subject.

7. The health management apparatus according to claim 6, wherein the output control unit performs control to output the coordinate region including the intersection point of the obesity parameter and the bone parameter of the similar subject in addition to the intersection point of the previous obesity parameter and the previous bone parameter of the target subject and the intersection point of the current obesity parameter and the current bone parameter of the target subject.

8. The health management apparatus according to claim 3, further comprising:
    a second search unit that searches for prescription information on an improved subject whose health condition is inversely changing to improvement in a case in which content of the change in the health condition of the target subject indicates deterioration,
    wherein the output control unit performs control to output the prescription information.

9. The health management apparatus according to claim 1, wherein the obesity parameter and the bone parameter are calculated on the basis of a radiographic image obtained by performing radiography for the target subject using a stacked radiation detector.

10. The health management apparatus according to claim 1, wherein the obesity parameter is any one of weight, a body-fat percentage, or a body mass index and the bone parameter is any one of bone mass or bone density.

11. The health management apparatus according to claim 1, wherein the target subject is a pet.

12. A method for operating a health management apparatus, the method comprising:
- an acquisition step of acquiring an obesity parameter indicating a degree of obesity of a target subject and a bone parameter indicating a degree of bone strength of the target subject;
- a first derivation step of deriving a health condition of the target subject on the basis of a correlation between the obesity parameter and the bone parameter; and
- an output control step of performing control to output the health condition,
- a reading step of reading, from a storage unit, a health condition table in which health conditions have been registered, each of the health conditions corresponding to one of a plurality of divided regions obtained by dividing a coordinate region in which the obesity parameter is disposed on one of a vertical axis and a horizontal axis and the bone parameter is disposed on the other axis, and outputting the health condition table,
- wherein, in the first derivation step, the health condition of the target subject is derived from the health condition table and corresponds to a divided region in which an intersection point of the obesity parameter and the bone parameter of the target subject is present.

13. A non-transitory computer-readable storage medium storing a program for operating a health management apparatus, the program causing a computer to function as:
- an acquisition unit that acquires an obesity parameter indicating a degree of obesity of a target subject and a bone parameter indicating a degree of bone strength of the target subject;
- a first derivation unit that derives a health condition of the target subject on the basis of a correlation between the obesity parameter and the bone parameter;
- an output control unit that performs control to output the health condition; and
- a reading unit that reads, from a storage unit, a health condition table in which health conditions have been registered, each of the health conditions corresponding to one of a plurality of divided regions obtained by dividing a coordinate region in which the obesity parameter is disposed on one of a vertical axis and a horizontal axis and the bone parameter is disposed on the other axis, and that outputs the health condition table to the first derivation unit,
- wherein the health condition of the target subject is derived by the first derivation unit from the health condition table and corresponds to a divided region in which an intersection point of the obesity parameter and the bone parameter of the target subject is present.

* * * * *